US010086354B2

(12) United States Patent
Gazit et al.

(10) Patent No.: US 10,086,354 B2
(45) Date of Patent: Oct. 2, 2018

(54) FORMATION OF ORGANIC NANOSTRUCTURE ARRAY

(71) Applicant: Ramot at Tel-Aviv University Ltd., Tel-Aviv (IL)

(72) Inventors: Ehud Gazit, Ramat-HaSharon (IL); Meital Reches, Beit-Hashmonai (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/482,867

(22) Filed: Apr. 10, 2017

(65) Prior Publication Data

US 2017/0209845 A1 Jul. 27, 2017

Related U.S. Application Data

(62) Division of application No. 12/312,961, filed as application No. PCT/IL2007/001495 on Dec. 4, 2007, now abandoned.

(60) Provisional application No. 60/872,499, filed on Dec. 4, 2006.

(51) Int. Cl.

| B81C 1/00 | (2006.01) |
| B01J 19/00 | (2006.01) |
| B82Y 30/00 | (2011.01) |
| C07K 5/065 | (2006.01) |
| C07K 17/14 | (2006.01) |
| B82Y 5/00 | (2011.01) |
| B82Y 15/00 | (2011.01) |
| B82Y 25/00 | (2011.01) |
| B82Y 40/00 | (2011.01) |

(52) U.S. Cl.
CPC ....... *B01J 19/0046* (2013.01); *B81C 1/00031* (2013.01); *B82Y 30/00* (2013.01); *C07K 5/06078* (2013.01); *C07K 17/14* (2013.01); *B01J 2219/00596* (2013.01); *B01J 2219/00709* (2013.01); *B01J 2219/00725* (2013.01); *B81B 2203/0361* (2013.01); *B81C 2201/0149* (2013.01); *B82Y 5/00* (2013.01); *B82Y 15/00* (2013.01); *B82Y 25/00* (2013.01); *B82Y 40/00* (2013.01); *Y10S 977/793* (2013.01); *Y10S 977/896* (2013.01)

(58) Field of Classification Search
None
See application file for complete search history.

(56) References Cited

U.S. PATENT DOCUMENTS

| 6,953,656 B2 | 10/2005 | Jacobson et al. |
| 7,879,212 B2 | 2/2011 | Yemini et al. |
| 2005/0170336 A1 | 8/2005 | Belcher et al. |
| 2008/0152839 A1 | 6/2008 | Han et al. |
| 2010/0291828 A1 | 11/2010 | Reches et al. |
| 2012/0021954 A1 | 1/2012 | Gazit et al. |

FOREIGN PATENT DOCUMENTS

| JP | 2003-331711 | 11/2003 | |
| JP | 2006-027945 | 2/2006 | |
| WO | WO 2004/052773 | 6/2004 | |
| WO | WO 2004/060791 | 7/2004 | |
| WO | WO 2005/000589 | 1/2005 | |
| WO | WO 2006/013552 | 2/2006 | |
| WO | WO-2006013552 A2 * | 2/2006 | ......... C07K 5/06078 |
| WO | WO 2006/027780 | 3/2006 | |
| WO | WO 2008/068752 | 6/2008 | |

OTHER PUBLICATIONS

Reches, Meital and Gazit, Ehud, "Casting metal nanowires within discrete self-assembled peptide nanotubes." Science (2003) 300 p. 625-627.*
Adler-Abramovich, Lihi et al, "Thermal and chemical stability if diphenylalanine peptide nanotubes: implications for nanotechnological applications." Langmuir (2006) 22 p. 1313-1320.*
Maslova, M. V. et al, "Surface properties of cleaved mica." Colloid J. (2004) 66(3) p. 322-328.*
Behrens, Sven H. and Grier, David J.; "The charge of glass and silica surfaces." J. Chem. Phys. (2001) 115(14) p. 6716-6721.*
Applicant-Initiated Interview Summary dated Dec. 8, 2015 From the US Patent and Trademark Office Re. U.S. Appl. No. 12/312,961.
Communication Pursuant to Article 94(3) EPC dated Mar. 11, 2015 From the European Patent Office Re. Application No. 07827468.5.
Communication Pursuant to Article 94(3) EPC dated May 16, 2014 From the European Patent Office Re. Application No. 07827468.5.
Communication Pursuant to Article 94(3) EPC dated Feb. 19, 2016 From the European Patent Office Re. Application No. 07827468.5.
Decision on Rejection dated Feb. 19, 2014 From the State Intellectual Property Office of the People's Republic of China Re. Application No. 2007800508820.0 and Its Translation Into English.
International Searching Report dated Sep. 15, 2008 From the International Searching Authority Re.: Application No. PCT/IL2007/001495.
Official Action dated Oct. 8, 2013 From the US Patent and Trademark Office. Re. U.S. Appl. No. 12/312,961.
Official Action dated Mar. 11, 2013 From the US Patent and Trademark Office Re. U.S. Appl. No. 12/312,961.
Official Action dated Jan. 19, 2017 From the US Patent and Trademark Office Re. U.S. Appl. No. 12/312,961. (9 pages).
Official Action dated Jan. 27, 2015 From the US Patent and Trademark Office Re. U.S. Appl. No. 12/312,961.
Official Action dated Aug. 28, 2014 From the US Patent and Trademark Office Re. U.S. Appl. No. 12/312,961.
Official Action dated Aug. 28, 2015 From the US Patent and Trademark Office Re. U.S. Appl. No. 12/312,961.
Restriction Official Action dated Dec. 11, 2012 From the US Patent and Trademark Office Re. U.S. Appl. No. 12/312,961.

(Continued)

*Primary Examiner* — Fred H Reynolds

(57) ABSTRACT

A nanostructure array is disclosed. The nanostructure array comprises a plurality of elongated organic nanostructures arranged generally perpendicularly to a plane.

4 Claims, 13 Drawing Sheets
(4 of 13 Drawing Sheet(s) Filed in Color)

(56) References Cited

OTHER PUBLICATIONS

Translation of Notice of Reason for Rejection dated Dec. 14, 2012 From the Japanese Patent Office Re. Application No. 2009-539870.
Translation of Office Action dated Nov. 20, 2012 From the State Intellectual Property Office of the People's Republic of China Re. Application No. 200780050882.0.
Translation of Office Action dated Sep. 20, 2011 From the State Intellectual Property Office of the People's Republic of China Re. Application No. 200780050882.0.
Written Opinion dated Sep. 15, 2008 From the International Searching Authority Re.: Application No. PCT/IL2007/001495.
Adler-Abramovich et al. "Self-Assembled Arrays of Peptide Nanotubes by Vapour Deposition", Nature Nanotechnology, 4(12):849-854, Published Online Oct. 18, 2009.
Banerjee et al. "Thiolated Peptide Nanotube Assembly as Arrays on Patterned Au Substrates", Nano Letters, XP002493885, 4(12): 2437-2440, Published on Web Nov. 20, 2004. Abstract, Figs.1-3.
Cox et al. "Magnetism in 4d-Transition Metal Clusters", Physical Review B, 49(17): 12295-12298, May 1, 1994.
Ghadiri et al. "Artificial Transmembrane Ion Channels From Self-Assembling Peptide Nanotubes", Nature, 369: 301-304, May 26, 1994.
Gladysz "Recoverable Catalysts. Ultimate Goals, Criteria of Evaluation, and the Green Chemistry Interface", Pure and Applied Chemistry, 73(8): 1319-1324, Jun. 2001.
Holowachuk et al. "Bovine Serum Albumin: cDNA Sequence and Expression", NCBI Database [Online], GenBank: AAA51411.1, Database Accession No. AAA51411, Feb. 11, 2002.
Hou et al. "Template-Synthesized Protein Nanotubes", Nano Letters, 5(2): 231-234, Published on Web Jan. 21, 2005.
Hyeon "Chemical Synthesis of Magnetic Nanoparticles", Chemical Communications, 8: 927-934, Published in Advance Dec. 3, 2002.
Kalifa et al. "Towards Micro-Machined Peptide Nanotube Based Devices", Digest of Technical Papers, Transducers '05, The 13th International Conference on Solid-State Sensors, Actuators and Microsystems, Seoul, Korea, Jun. 5-9, 2005, IEEE, XP010828743, 2: 1509-1512, Jun. 5, 2005. Abstract, p. 1509, col. 1, Last §, col. 2, § 2, p. 1510, col. 1, § 2.
LaMer et al. "Theory, Production and Mechanism of Formation of Monodispersed Hydrosols", Journal of the American Chemical Society, JACS, 72(11): 4847-4854, Nov. 17, 1950.
Masson et al. "Rapid FTIR Method for Quantification of Styrene-Butadiene Type Copolymers in Bitunen", Journal of Applied Polymer Science, 79: 1034-1041, 2001.
Meltzer et al. "Investigating Nanorobotics and Nanostructure Formation With AFM Nanomanipulation", Veeco Instruments Sales Literature, 8 P., 2003.
Motesharei et al. "Diffusion-Limited Size-Selective Ion Sensing Based on SAM-Supported Peptide Nanotubes", Journal of the American Chemical Society, XP002493887, 119(46): 11306-11312, Nov. 19, 1997. Abstract, Fig.3.
Pavanetto et al. "Spray-Dried Albumin Microspheres for the Intra-Articular Delivery of Dexamethasone", Journal of Microencapsulation, 11(4): 445-454, 1994.
Planeix et al. "Applications of Carbon Nanotubes as Supports in Heterogeneous Catalysis", Journal of the American Chemical Society, 116: 7935-7936, 1994.
Qiu et al. "Sol-Gel Assisted ZnO Nanorod Array Template to Synthesize $TiO_2$ Nanotube Arrays", Nanotechnology, 17: 4695-4698, Aug. 30, 2006.
Reches et al. "Amyloid Fibril Formation by Pentapeptide and Tetrapeptide Fragments of Human Calcitonin", The Journal of Biological Chemistry, 277(38): 35475-35480, Sep. 20, 2002.
Reches et al. "Casting Metal Nanowires Within Discrete Self-Assembled Peptide Nanotubes", Science, 300: 625-627, Apr. 25, 2003.
Reches et al. "Controlled Patterning of Aligned Self-Assembled Peptide Nanotubes", Nature Nantechnology, XP002493888, 1(3): 195-200, Dec. 2006.
Reches et al. "Formation of Closed-Cage Nanostructures by Self-Assembly of Aromatic Dipeptides", Nano Letters, 4(4): 581-585, 2004.
Schellenberger et al. "Magneto/Optical Annexin V, A Multimodal Protein", Bioconjugate Chemistry, 15: 1062-1067, 2004.
Shibue et al. "Effect of Anionic Ion-Pairing Reagent Hydrophobicity on Selectivity of Peptide Separations by Reversed-Phase Liquid Chromatography", Journal of Chromatography A, 1080: 68-75, Published Online Apr. 20, 2005.
Song et al. "Synthesis of Peptide-Nanotube Platinum-Nanoparticle Composites", Chemical Communications, 2004: 1044-1045, Published in Advance Apr. 6, 2004.
Sotiropoulou et al. "Carbon Nanotube Array-Based Biosensor", Analytical and Bioanalytical Chemistry, 375(1): 103-105, Published Online Oct. 31, 2002.
Zhang et al. "Development in Nanoparticle Assembly Technology Research", Journal of Shijiazhuang University, 8(3): 28-31, May 31, 2006. & English Translation.
Zhao et al. "Simultaneous Targeted Immobilization of Anti-Human IgG-Coated Nanotubes and Anti-Mouse IgG-Coated Nanotubes on the Complementary Antigen-Patterned Surfaces Via Biological Molecular Recognition", Journal of the American Chemical Society, XP002493886, 127(25): 8930-8931, 2005. Abstract, Figs.1-2.

\* cited by examiner

Fig. 8a
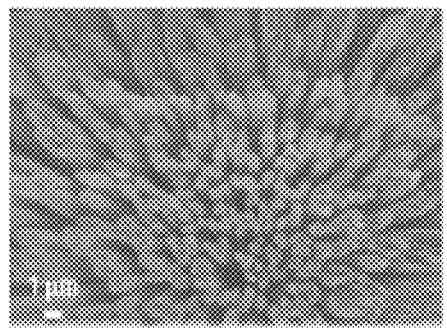
Fig. 8b
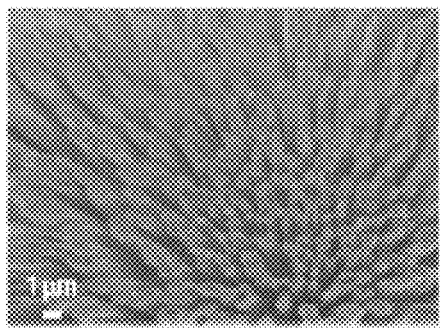
Fig. 8c
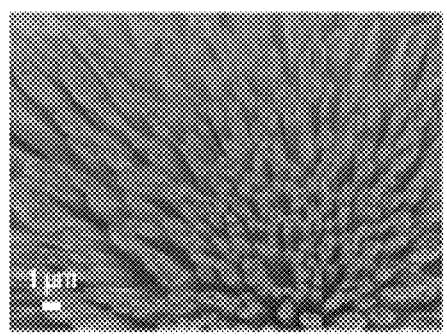
Fig. 8d
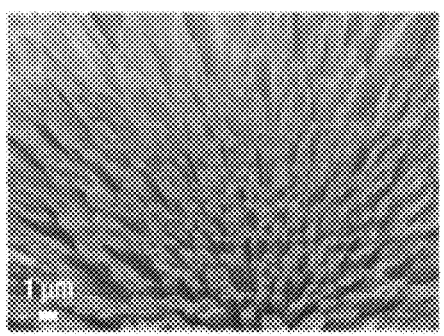
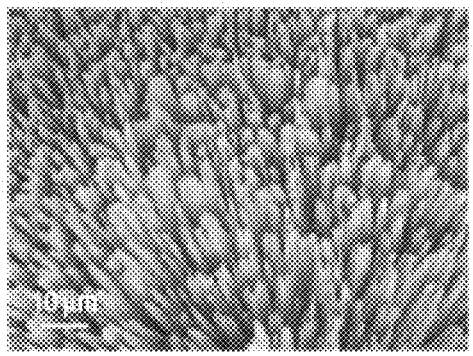
Fig. 9a
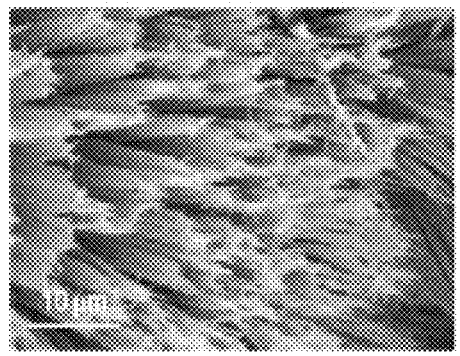
Fig. 9b
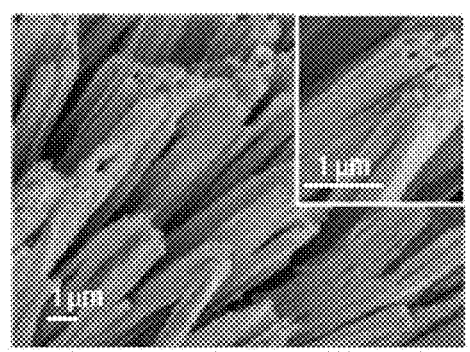
Fig. 9c

FORMATION OF ORGANIC NANOSTRUCTURE ARRAY

RELATED APPLICATIONS

This application is a division of U.S. patent application Ser. No. 12/312,961 filed on Aug. 18, 2011 which is a National Phase Application of PCT Application No. PCT/IL2007/001495 having International Filing Date of Dec. 4, 2007, which claims the benefit of priority of U.S. Provisional Patent Application No. 60/872,499, filed on Dec. 4, 2006. The contents of the above applications are all incorporated by reference as if fully set forth herein in their entirety.

FIELD AND BACKGROUND OF THE INVENTION

The present invention, in some embodiments thereof, relates to nanostructures and, more particularly, but not exclusively, to peptide nanostructures.

Peptide nanostructures and various applications thereof are described in International Patent Application, Publication Nos. WO2004/052773, WO2004/060791, WO2005/000589, WO2006/027780 and WO2006/013552, all assigned to the same assignee as the present application and being incorporated by reference by their entirety.

Generally, peptide nanostructures can posses many ultra-structural and physical similarities to carbon nanotubes. Known peptide nanostructures are made by self assembly of aromatic dipeptides, such as diphenylalanine. The assembled dipeptides form ordered assemblies of various structures with persistence length on the order of micrometers.

For industrial applications, self-assembled peptide nanostructures are favored over carbon nanotubes from standpoint of cost, production means and availability. Additionally, peptides nanostructures can be used as organic building blocks for bio-nanotechnology owing to their biocompatibility, chemical flexibility and versatility, biological recognition abilities and facile synthesis [Reches, M. and Gazit, E. Casting metal nanowires within discrete self-assembled peptide nanotubes. Science 300, 625-627 (2003)].

Peptide nanostructures have been proposed to be used in various technological applications, such as microelectronics, magnetic recording systems, chemical sensors, displays systems, memory media, electron-emission lithography and thermoelectric systems.

SUMMARY OF THE INVENTION

An aspect of some embodiments of the present invention relates to a nanostructure array which comprises a plurality of elongated organic nanostructures arranged in an ordered arrangement. In various exemplary embodiments of the invention the elongated organic nanostructures are aligned generally parallel to each other. In some embodiments, the nanostructures are arranged generally perpendicularly on a substrate. In other embodiments, the nanostructures are arranged generally parallel to a substrate.

An aspect of some embodiments of the present invention relates to a method suitable for fabricating a nanostructure array.

According to some embodiments of the present invention, organic monomers dissolved in an organic volatile solvent are dispensed on a substrate. In some embodiments of the present invention the organic volatile solvent is selected so as to allow dispersion of the organic monomers in the solution prior to the evaporation. While generating conditions for self assembling of the organic monomers, the solvent is evaporated and the organic monomers remain on the substrate in a self-assembled form. In some embodiments of the present invention once the solvent is evaporated elongated organic nanostructures are formed on the substrate, generally perpendicularly thereto.

According to some embodiments of the present invention, organic monomers and nanoparticles are incubated under conditions for self assembling of the organic monomers to elongated organic nanostructures and self coating of the elongated organic nanostructures by the nanoparticles. In various exemplary embodiments of the invention the nanoparticles are responsive to a force field. For example, the nanoparticles can be magnetic nanoparticles in which case the force field is preferably a magnetic field. The nanoparticles can be electrically charged, in which case the force field is preferably an electric field. The force field is applied to the coated nanostructures such as to align the nanostructures generally parallel to each other.

In some embodiments of the present invention the organic monomers and/or the nanostructures are electrically charged. The monomers and/or substrate are preferably selected to establish repulsion forces among the nanostructures and optionally between the nanostructures and the substrate. For example, the outer walls of the nanostructures can be positively charge. Such configuration can facilitates formation of a nanostructure array which is generally perpendicular to a plane.

In various exemplary embodiments of the invention the organic nanostructures are peptide nanostructures. In some embodiments of the present invention each of the peptide nanostructures comprise peptides which comprise from 2 to 15 amino acid residues. For example, one or more of the peptides can be a dipeptide, such as, but not limited to, a phenylalanine-phenylalanine dipeptide. In some embodiments, the peptides comprise one or more aromatic amino acid residue. For example, one or more of the peptides can consists essentially of aromatic amino acid residues. In some embodiments, one or more of the peptides is an end-capping modified peptide. In some embodiments, one or more of the peptide nanostructure comprises a functional group attached thereto.

The nanostructure array of the present embodiments can be integrated and used in many applications, including, without limitation, multi-array sensors, field emission devices, nano-mechanic systems, nano-electromechanic systems and nano-fluidic systems.

Thus, for example, the nanostructure array of the present embodiments can be used in a field effect transistor (FET), whereby the nanostructure array can serve, e.g., as a channel interconnecting a source and a drain. Of particular advantage is the embodiment in which the nanostructures are aligned vertically to the other electrodes of the FET.

The nanostructure array of the present embodiments can also serve as a conductive layer for multiple conductors in an integrated circuit chip. The conductive layer can be constructed, for example, as a stack of multiple sublayers in which one or more sublayers comprise oriented nanostructures. Different sublayers can include nanostructures which are oriented to different directions.

The nanostructure array of the present embodiments can also be incorporated in sensing and/or stimulating devices, for example, a medical lead. This embodiment is particularly useful when the nanostructures are vertically aligned. Such medical lead can have improved electrode performance due to the high surface area of the nanostructure array. The medical lead can be used for cardiac pacing and/or sensing, brain stimulations and/or sensing and the like.

The nanostructure array of the present embodiments can also used for transporting thermal energy to or from an object. An array of nanostructures can be aligned, preferably vertically, on a surface of a substrate having high thermal conductivity. The nanostructures can be exposed to the environment so as to evacuate heat from or to the substrate. Thus, the nanostructure array of the present embodiments can serve as a heat sink.

The nanostructure array of the present embodiments can also be used in various sensors, including, without limitation, electrochemical sensors, mechanical sensors, electromechanical sensors and the like. For example, a sensor incorporating the nanostructure array of the present embodiments can be used to monitor strain, pressure or temperature changes experienced by a static or dynamic structure to which the sensor is coupled. A sensor incorporating the nanostructure array of the present embodiments can also operate according to the principles of quartz crystal microbalance (QCM) sensors for the detection and measurements of low-mass objects, e.g., bacteria or the like.

Due to its large surface area, the nanostructure array of the present embodiments can also be used for collecting analytes from a fluidic medium (gas or liquid), and for concentrating the analytes, e.g., for spectroscopy (e.g. Fourier transform spectroscopy, Fourier transform infrared spectroscopy, etc.)

According to an aspect of some embodiments of the present invention there is provided a nanostructure array. The nanostructure array comprises a substrate and a plurality of elongated organic nanostructures arranged generally perpendicularly on the substrate.

According to an aspect of some embodiments of the present invention there is provided a nanostructure array, comprising a planar arrangement of a plurality of elongated organic nanostructures aligned generally parallel to each other.

According to an aspect of some embodiments of the present invention there is provided a field effect transistor, comprising the nanostructure array described herein.

According to an aspect of some embodiments of the present invention there is provided a conductive layer, comprising the nanostructure array described herein.

According to an aspect of some embodiments of the present invention there is provided a sensor comprising the nanostructure array of any described herein.

According to an aspect of some embodiments of the present invention there is provided a medical lead comprising the nanostructure array described herein.

According to an aspect of some embodiments of the present invention there is provided a stimulating electrode comprising the nanostructure array described herein.

According to an aspect of some embodiments of the present invention there is provided a device for transferring thermal energy, comprising the nanostructure array described herein.

According to an aspect of some embodiments of the present invention there is provided an analyte collecting device, comprising the nanostructure array described herein.

According to an aspect of some embodiments of the present invention there is provided a method of fabricating a nanostructure array, comprising dispensing on a substrate organic monomers dissolved in an organic volatile solvent, and evaporating the solvent while generating conditions for self assembling of the organic monomers such as to form a plurality of elongated organic nanostructures arranged generally perpendicularly on the substrate.

According to some embodiments of the present invention the organic volatile solvent is selected so as to allow dispersion of the organic monomers in the solvent prior to the evaporation.

According to some embodiments of the present invention the organic monomers are peptide monomers dissolved in the organic volatile solvent at a concentration of at least 10 mg/ml According to some embodiments of the present invention the organic monomers are electrically charged.

According to an aspect of some embodiments of the present invention there is provided a method of fabricating a nanostructure array. the method comprises: incubating organic monomers and nanoparticles being responsive to a force field under conditions for self assembling of the organic monomers to elongated organic nanostructures and self coating of the elongated organic nanostructures by the nanoparticles; and applying a force field to the elongated organic nanostructures such as to align the elongated organic nanostructures generally parallel to each other.

According to some embodiments of the present invention the nanoparticles are magnetic nanoparticles and the force field is a magnetic field.

According to some embodiments of the present invention the nanoparticles are electrically charged nanoparticles and the force field is an electric field.

According to some embodiments of the present invention the organic monomers comprise peptide monomers.

According to some embodiments of the present invention the organic nanostructures are multi-walled nanostructures.

According to some embodiments of the present invention the organic nanostructures are peptide nanostructures.

According to some embodiments of the present invention the peptide nanostructures comprises a plurality of peptides.

According to some embodiments of the present invention each peptide comprises from 2 to 15 amino acid residues.

According to some embodiments of the present invention each peptides comprises at least one aromatic amino acid residue.

According to some embodiments of the present invention at least one peptide is an end-capping modified peptide.

According to some embodiments of the present invention at least one peptide consists essentially of aromatic amino acid residues.

According to some embodiments of the present invention at least one peptide is a dipeptide.

According to some embodiments of the present invention each peptide is a phenylalanine-phenylalanine dipeptide.

According to some embodiments of the present invention at least one of the peptide nanostructures is coated by at least one layer of nanoparticles, which can be magnetic nanoparticles and/or they can be electrically charged.

According to some embodiments of the present invention at least one peptide nanostructure comprises a functional group attached thereto.

According to some embodiments of the present invention the organic nanostructures are electrically charged.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1a-1c are schematic illustrations of a nanostructure array, according to various exemplary embodiments of the present invention.

FIG. 2 is a schematic cross-sectional illustration of a transistor according to an embodiment of the present invention.

FIG. 3 is a schematic illustration of a conductive layer, according to various exemplary embodiments of the present invention.

FIGS. 4a-4b are schematic illustrations of medical leads, according to various exemplary embodiments of the present invention.

Figure 5:
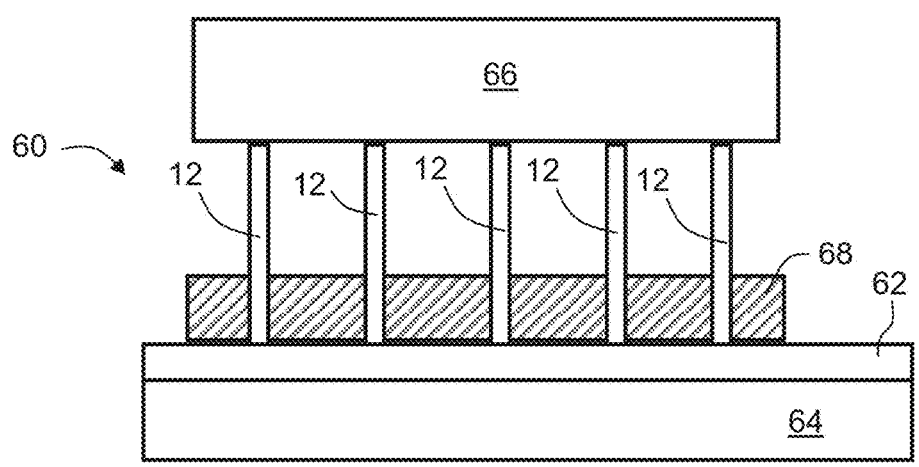

FIG. 5 schematically illustrates a device for transporting thermal energy to or from an object, according to various exemplary embodiments of the present invention.

Figure 6:
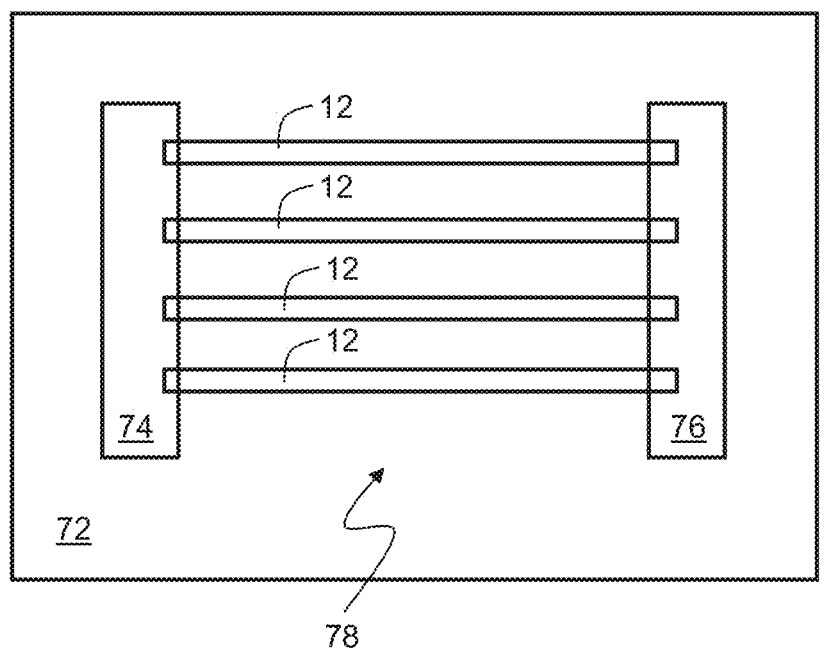

FIG. 6 is a schematic illustration of a sensor system according to various exemplary embodiments of the present invention.

FIGS. 7a-7f present vertically aligned diphenylalanine-based nanotubes self-assembled into peptide nanoforest; (a) a possible model for the formation of the aligned peptide nanotubes array. Applying the dipeptide monomers dissolved in the organic solvent onto siliconized glass resulted in the formation of a vertically aligned array of peptide nanotubes. (b) SEM analysis of the vertically aligned peptide nanotubes. (c) Cold-Field Emission Gun High Resolution Scanning Electron Microscope (CFEG-HRSEM) analysis of the nanotubes array. The inset represents higher magnification of the aligned nanotubes. (d) High magnification micrograph (×120,000) of one individual nanotube of the array obtained by CFEG-HRSEM. (e) X-ray diffractogram of a peptide array of a glass surface. (f) Electron-diffraction analysis of a single peptide nanotube. Axis a is oriented normal to the long axis of the crystal.

FIGS. 8a-8d are images showing Cold-Field Emission Gun High Resolution Scanning Electron Microscope (CFEG-HRSEM) analysis with various tilting angles of the diphenylalanine-based peptide nanotubes array assembled on a siliconized glass. Micrographs were taken for the same area in the sample while the angle of the sample was continuously changed. The following tilting angles were viewed: (a) Tilting angle of 10°. (b) 20°. (c) 30° (d) 40°. The scale bar represents 1 µm.

FIGS. 9a-9c are images showing (a) SEM micrograph of the narrower assemblies aligned on siliconized glass. (b) Higher SEM magnification of the assembled tubular structures. (c) CFEG-HRSEM analysis of the self-assembled tubular structures; the inset represents higher magnification.

Figure 10A:
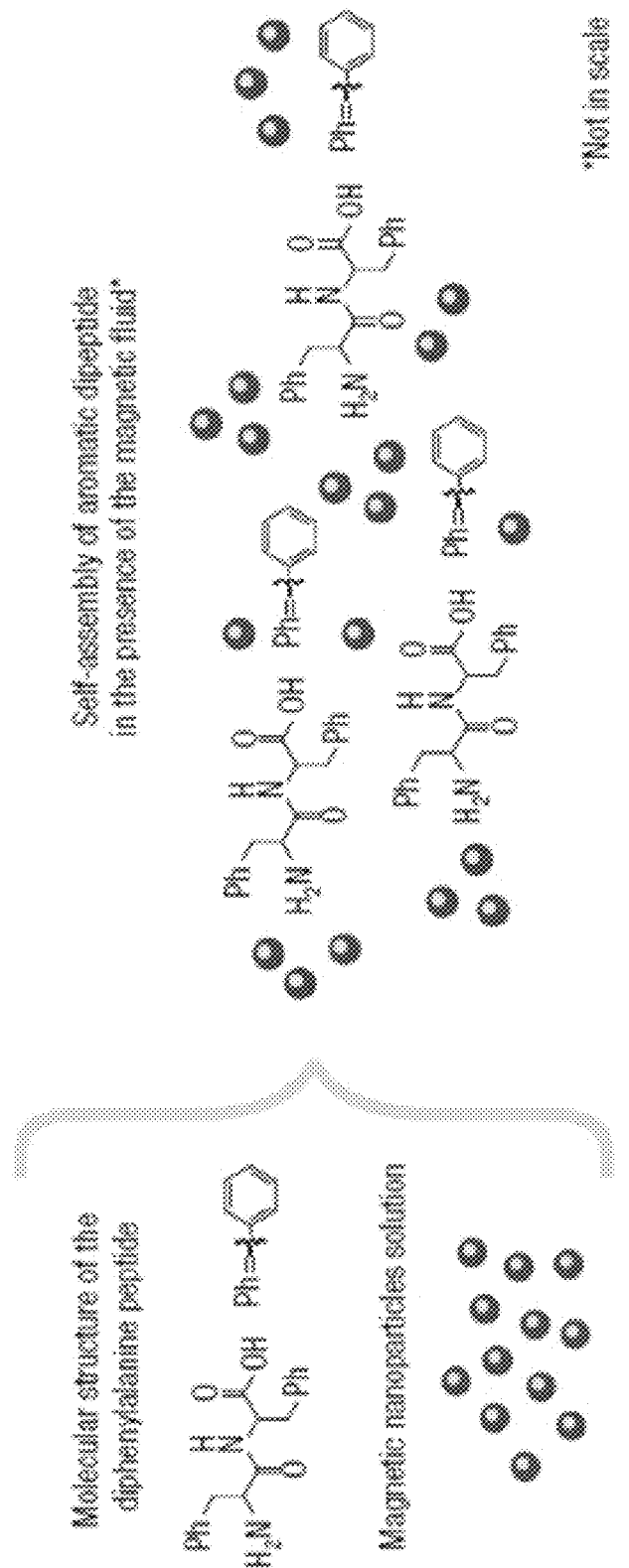
Figure 10B:
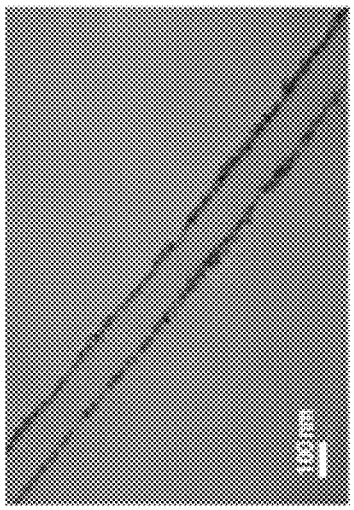

FIG. 10a is a schematic illustrating of dipeptide monomers self-assembled in the presence of ferrofluid solution containing magnetite nanoparticles, according to various exemplary embodiments of the present invention FIG. 10b is a TEM image of a self-assembled peptide nanostructure coated with magnetic particles.

Figure 10C:
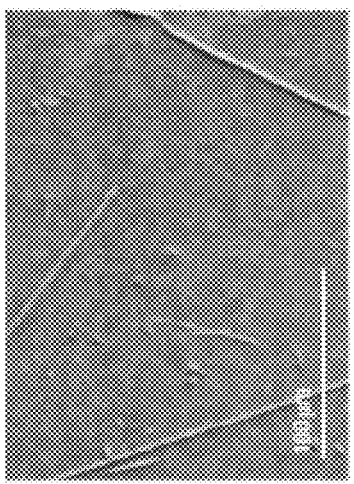

FIG. 10c is a low-magnification SEM micrograph of self-assembled coated peptide nanostructures.

Figure 10D:
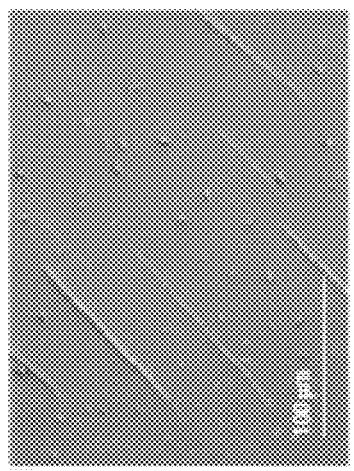

FIG. 10d is a low-magnification SEM micrograph showing horizontal arrangement of the self-assembled coated peptide nanostructures of FIG. 10c.

Figure 10E:
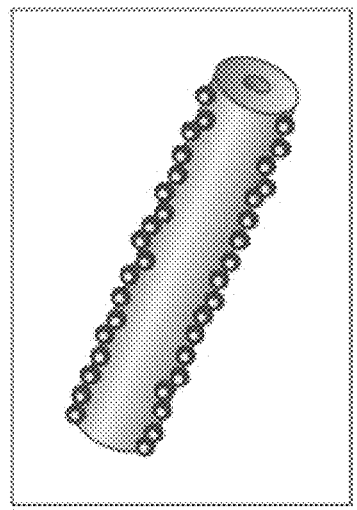
Figure 10F:
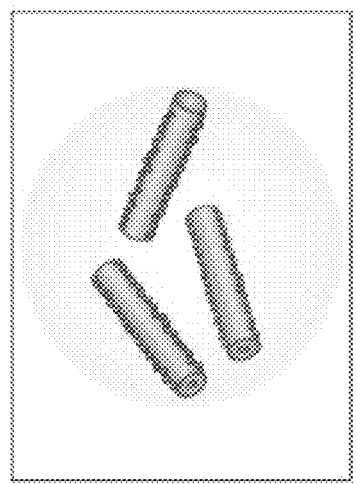
Figure 10G:
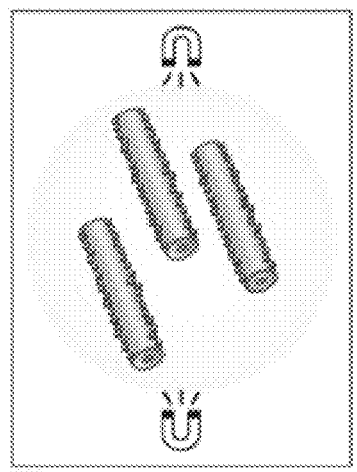

FIGS. 10e-10g are schematic representation of a self-assembled nanostructure, (f) several randomly oriented nanostructures, and (g) horizontally aligned nanostructures upon and following their exposure to a magnetic field.

Figure 11:
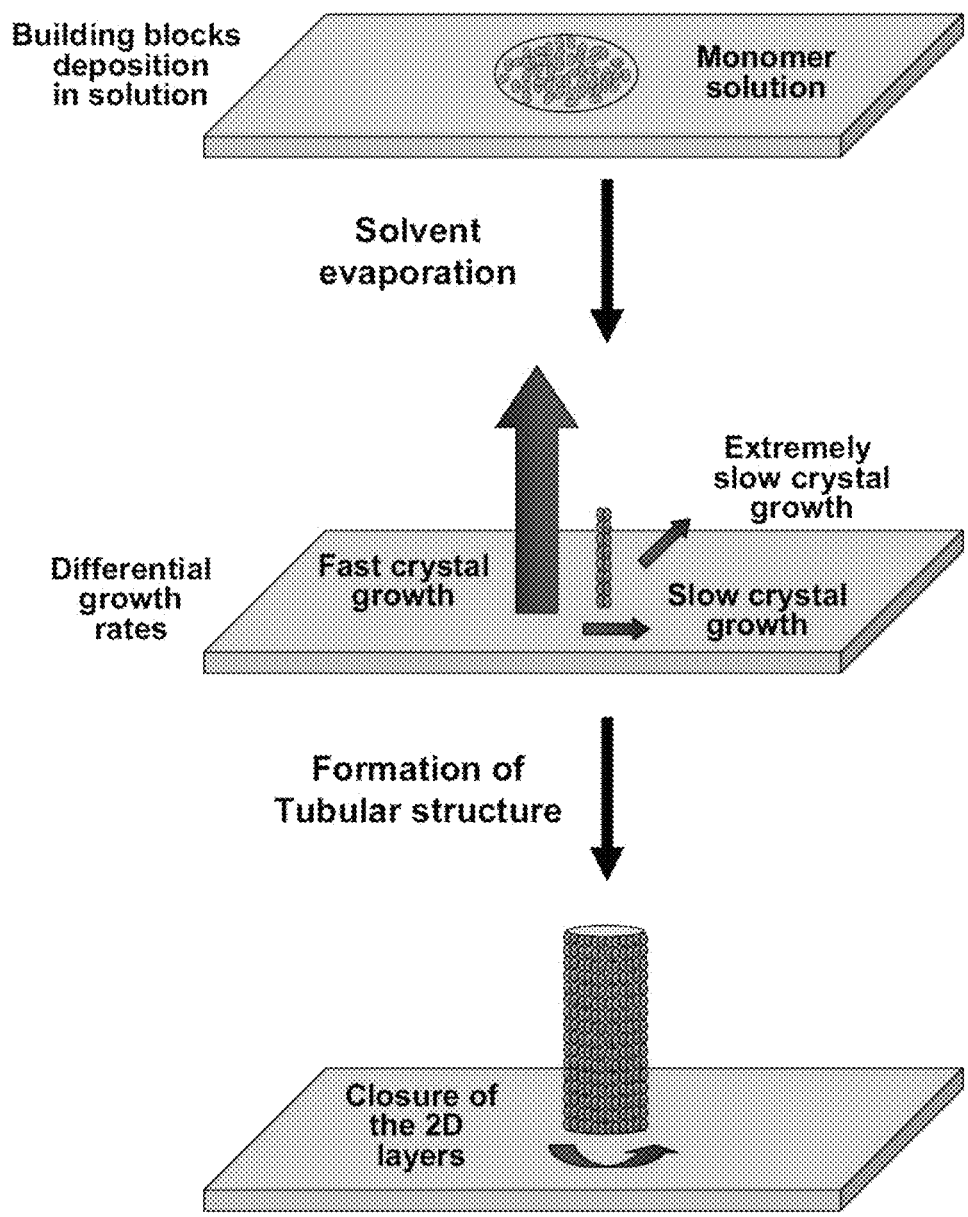

FIG. 11 presents a model for the formation of the nanostructures of the present embodiments. The peptide building blocks are being deposited as monomers in HFP solution. The rapid evaporation leads to supersaturation and crystallization process. The differential growth rates at the different directions lead to the formation of elongated sheets. The two dimensional elongated sheets tend to form close tubular structures.

FIGS. 12a-12f are SEM images demonstrating the formation of an aligned nanotubes array with various peptide concentrations. The following peptide concentrations are presented: (a) 20 mg/ml. (b) 40 mg/ml. (c) 60 mg/ml. (d) 80 mg/ml. (e) 120 mg/ml. (f) 180 mg/ml.

FIGS. 13a-13e are images showing SEM analysis of diphenylalanine peptide analogues self-assembled onto a siliconized glass in the same manner as the "wild-type" dipeptide. The following dipeptides were examined: (a) Ac-Phe-Phe-NH$_2$. (b) t-Butyl carbamate-Phe-Phe-COOH (Boc-Phe-Phe-COOH) (c) Carbobenzyloxy-Phe-Phe-COOH (Cbz-Phe-Phe-COoH) (d) Fluorenylmethoxycarbonyl-Phe-Phe-COOH (Fmoc-Phe-Phe-COOH) (e) Cyclo-Phe-Phe.

FIGS. 14a-14d are images showing SEM analysis micrograph of the diphenylalanine peptide self-assembled on a siliconized glass in the presence of a base. (a) 0.5% DIAE. (b) 1% DIAE. (c) 2% DIAE. (d) 5% DIAE.

DESCRIPTION OF SPECIFIC EMBODIMENTS OF THE INVENTION

The present invention, in some embodiments thereof, relates to nanostructures and, more particularly, but not exclusively, to peptide nanostructures.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1A:
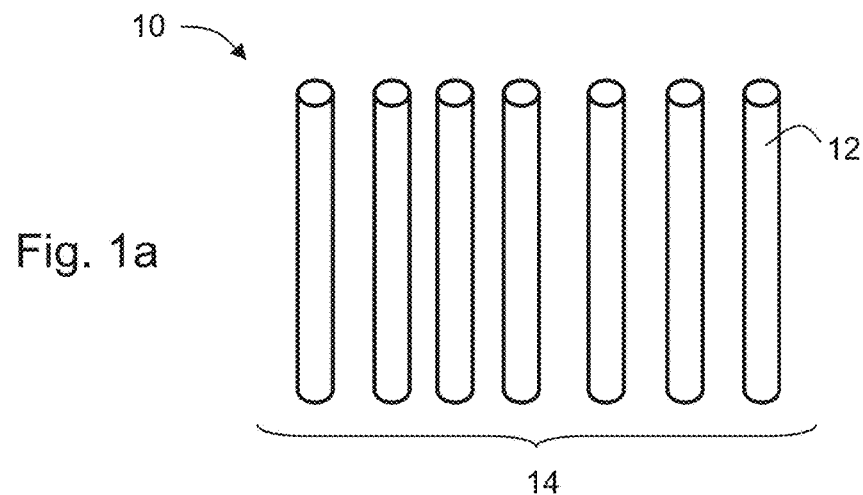
Figure 1B:
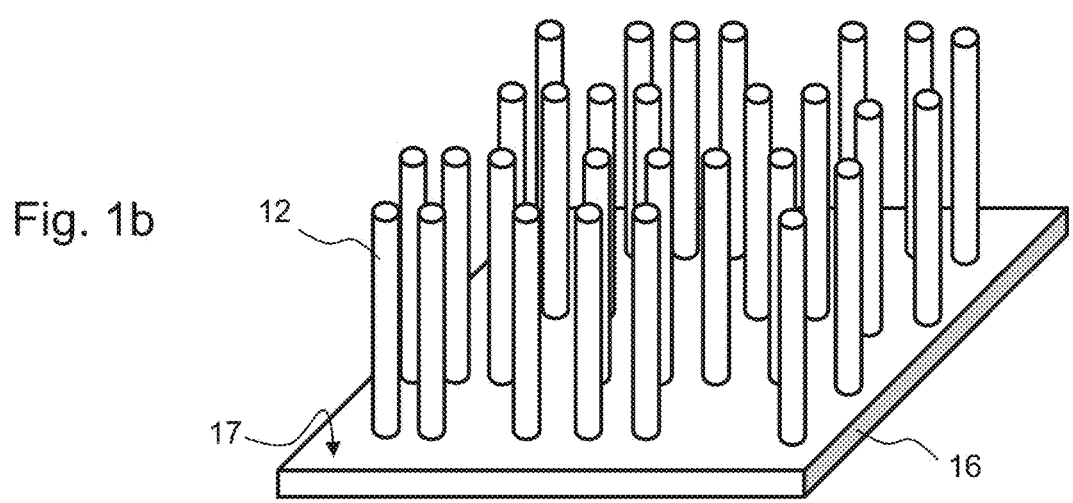
Figure 1C:
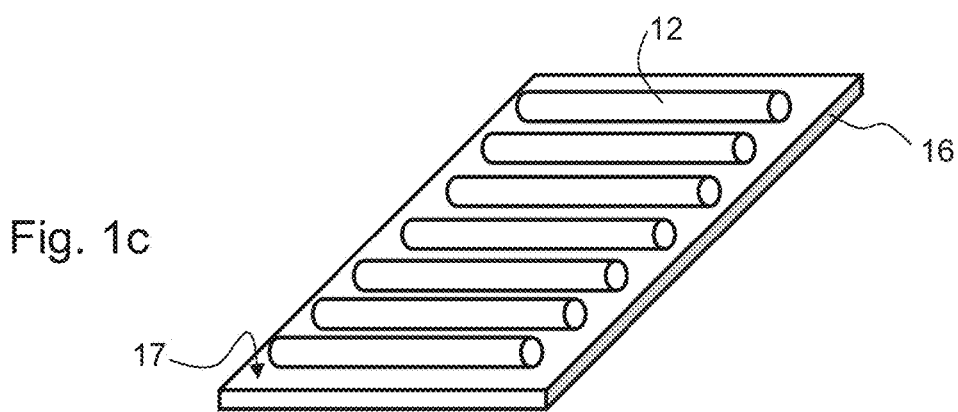

FIGS. 1a-1c are schematic illustrations of a nanostructure array 10, according to various exemplary embodiments of the present invention. Nanostructure array 10 comprises a plurality of elongated organic nanostructures 12 arranged in an ordered arrangement 14.

As used herein the phrase "elongated nanostructure" refers to a structure having a diameter of less than 1 µm (preferably less than 500 nm, more preferably less than about 50 nm, even more preferably less than about 10 nm), and length of at least 1 μm, more preferably at least 10 nm, even more preferably at least 100 nm and even more preferably at least 500 nm.

The phrase "organic nanostructure" refers to a nanostructure made at least in part of organic substance. As used herein, the phrase "organic substance" describes any substance that comprises carbon and hydrogen atoms, with or without additional elements.

Ordered arrangement 14 is typically, but not obligatorily, an arrangement in which organic nanostructures 12 are aligned generally parallel to each other. Nanostructures 12 can engage a single plane, thus forming a "monolayer" of nanostructures), or they can engage a plurality planes or a bulk, thus forming a "forest" of nanostructures). For example, in some embodiments of the present invention nanostructures in array 10 are arranged on a substrate 16 generally perpendicularly.

The term "generally perpendicularly" refers to an angular relationship between nanostructures 12 and a plane, e.g., surface 17 of substrate 16. The nanostructures are said to be generally perpendicular to the plane if the angle between the nanostructures and the normal to the plane is, on the average, less than 20°, more preferably less than 10°, more preferably less than 5°, more preferably, but not obligatorily, less than 2°.

In other embodiments, the nanostructures are arranged generally parallel to substrate 16.

The term "generally parallel" also refers to the angular relationship between nanostructures 12 and a plane, e.g., surface 17 of substrate 16. The nanostructures are said to be generally parallel to the plane if the angle between the nanostructures and the normal to the plane is, on the average, from about 80° to about 90°, more preferably from about 85° to about 90°, more preferably, but not obligatorily, from about 88° to about 90°.

Nanostructures 12 are typically shaped as tubular structures. The tubular structure of nanostructures 12 can be hollow, or it can be filled with a filler material, such as, but not limited to, a conducting material, a semiconducting material, a thermoelectric material, a magnetic material (paramagnetic, ferromagnetic or diamagnetic), a light-emitting material, a biomineral, a polymer and/or an organic material. The filler material can be either in a condensed or in a gaseous state. Nanostructures 12 can also be coated by a coating material which can also be conducting, semiconducting, thermoelectric, magnetic, light-emitting, biomineral, polymer and/or organic.

In various exemplary embodiments of the invention nanostructures 12 have a thick wall or a multi-walled structure. This is realized as relatively large ratio between the outer diameter and the diameter of the interior cavity of nanostructures 12. In some embodiments of the present invention the ratio between the outer and inner diameters of nanostructures 12, is at least 1.5, more preferably at least 2.

The density of nanostructures in the array is preferably high. For example, when the array is generally perpendicular to a plane (see FIG. 1b), there is preferably at least 1 nanostructures per square micron, or at least 2 nanostructures per square micron, or at least 3 nanostructures per square micron, or at least 4 nanostructures per square micron, or at least 5 nanostructures per square micron. Higher densities, such as, but not limited to, 10, 11, 12, 13 or more nanostructures per square micron are also contemplated. In experiments performed by the inventors of the present invention a density of 10-20 nanostructures per 100 square microns was obtained (see FIGS. 7b and 7c in the examples section that follows). In other experiments performed by the inventors of the present invention a density of 10 nanostructures per square micron was obtained (see FIGS. 9a-c).

In various exemplary embodiments of the invention the number of nanostructures in array 10 is large. Typically, but not obligatorily, there are more than 10, more preferably a few tens (e.g., 20, 30, 40, 50 or more) of nanostructures in the array. In some embodiments there are 100, or, more preferably, but not obligatorily, a few hundreds (e.g., 200, 300, 400, 500 or more) nanostructures in the array.

In various exemplary embodiments of the invention nanostructures 12 are peptide nanostructures.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

The peptides forming the nanostructures of the present embodiments typically comprise from 2 to 15 amino acid residues. More preferably, the peptides are short peptides of less than 10 amino acid residues, more preferably less than 8 amino acid residues and more preferably are peptides of 2-6 amino acid residues, and hence each peptide preferably has 2, 3, 4, 5, or 6 amino acid residues.

As used herein the phrase "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Natural aromatic amino acids, Trp, Tyr and Phe, may be substituted for synthetic non-natural acid such as Phenylglycine, TIC, napthylalanine (Nal), phenylisoserine, threoninol, ring-methylated derivatives of Phe, halogenated derivatives of Phe or O-methyl-Tyr and □-amino acids.

The peptides of the present embodiments may include one or more modified amino acids or one or more non-amino acid monomers (e.g. fatty acids, complex carbohydrates etc).

The peptides utilized for forming the nanostructures of the present embodiments are typically linear peptides. Yet, cyclic forms of the peptide are not excluded from the scope of the present invention.

In some embodiments of the present invention the peptides composing the peptide nanostructures of the present embodiments comprise one or more aromatic amino acid residue. The advantage of having such peptides is that the aromatic functionalities which are built into the peptide allow the various peptide building blocks to interact through attractive aromatic interactions, to thereby form the nanostructure.

The phrase "aromatic amino acid residue", as used herein, describes an amino acid residue that has an aromatic moiety, as defined herein, in its side-chain.

Thus, according to some embodiments of the present invention, each of the peptides composing the peptide nanostructures comprises the amino acid sequence X—Y or Y—X, wherein X is an aromatic amino acid residue and Y is any other amino acid residue.

The peptides of the present invention, can be at least 2 amino acid in length.

In some embodiments of the present invention, one or several of the peptides forming the nanostructures is a polyaromatic peptide, which comprises two or more aromatic amino acid residues.

As used herein the phrase "polyaromatic peptides" refers to peptides which include at least 80%, more preferably at least 85%, more preferably at least 90%, more preferably at least 95% or more aromatic amino acid residues. In some embodiments, at least one peptide consists essentially of aromatic amino acid residues. In some embodiments, each peptide consists essentially of aromatic amino acid residues.

Thus for example, the peptides used for forming the nanostructures can include any combination of: dipeptides composed of one or two aromatic amino acid residues; tripeptides including one, two or three aromatic amino acid residues; and tetrapeptides including two, three or four aromatic amino acid residues and so on.

In some embodiments of the present invention, the aromatic amino acid can be any naturally occurring or synthetic aromatic residue including, but not limited to, phenylalanine, tyrosine, tryptophan, phenylglycine, or modificants, precursors or functional aromatic portions thereof.

In some embodiments, one or more peptides in the plurality of peptides used for forming the nanostructures include two amino acid residues, and hence is a dipeptide.

In some embodiments, each of the peptides used for forming the nanostructures comprises two amino acid residues and therefore the nanostructures are formed from a plurality of dipeptides.

Each of these dipeptides can include one or two aromatic amino acid residues. Preferably, but not obligatorily each of these dipeptides includes two aromatic amino acid residues. The aromatic residues composing the dipeptide can be the same, such that the dipeptide is a homodipeptide, or different. Preferably, the nanostructures are formed from homodipeptides.

Hence, in various exemplary embodiments of the invention each peptide in the plurality of peptides used for forming the nanostructures is a homodipeptide composed of two aromatic amino acid residues that are identical with respect to their side-chains residue.

The aromatic amino acid residues used for forming the nanostructures can comprise an aromatic moiety, where the phrase "aromatic moiety" describes a monocyclic or polycyclic moiety having a completely conjugated pi-electron system. The aromatic moiety can be an all-carbon moiety or can include one or more heteroatoms such as, for example, nitrogen, sulfur or oxygen. The aromatic moiety can be substituted or unsubstituted, whereby when substituted, the substituent can be, for example, one or more of alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

Exemplary aromatic moieties include, for example, phenyl, biphenyl, naphthalenyl, phenanthrenyl, anthracenyl, [1,10] phenanthrolinyl, indoles, thiophenes, thiazoles and, [2,2']bipyridinyl, each being optionally substituted. Thus, representative examples of aromatic moieties that can serve as the side chain within the aromatic amino acid residues described herein include, without limitation, substituted or unsubstituted naphthalenyl, substituted or unsubstituted phenanthrenyl, substituted or unsubstituted anthracenyl, substituted or unsubstituted [1,10] phenanthrolinyl, substituted or unsubstituted [2,2']bipyridinyl, substituted or unsubstituted biphenyl and substituted or unsubstituted phenyl.

The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine. When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

Representative examples of homodipeptides that can be used to form the nanostructures of the present embodiments include, without limitation, a naphthylalanine-naphthylalanine dipeptide, phenanthrenylalanine-phenanthrenylalanine dipeptide, anthracenylalanine-anthracenylalanine dipeptide, [1,10] phenanthrolinylalanine-[1,10] phenanthrolinylalanine dipeptide, [2,2']bipyridinylalanine-[2,2']bipyridinylalanine dipeptide, (pentahalo-phenylalanine)-(pentahalo-phenylalanine) dipeptide, phenylalanine-phenylalanine dipeptide, (amino-phenylalanine)-(amino-phenylalanine) dipeptide, (dialkylamino-phenylalanine)-(dialkylamino-phenylalanine) dipeptide, (halophenylalanine)-(halophenylalanine) dipeptide, (alkoxy-phenylalanine)-(alkoxy-phenylalanine) dipeptide, (trihalomethyl-phenylalanine)-(trihalomethyl-phenylalanine) dipeptide, (4-phenyl-phenylalanine)-(4-phenyl-phenylalanine) dipeptide and (nitro-phenylalanine)-(nitro-phenylalanine) dipeptide.

According to various exemplary embodiments of the present invention the peptide nanostructures are composed from a plurality of diphenylalanine (Phe-Phe) homodipeptides.

In some embodiments of the present invention one or more peptides in the plurality of peptides used to form the nanostructures is an end-capping modified peptide.

The phrase "end-capping modified peptide", as used herein, refers to a peptide which has been modified at the N-(amine)terminus and/or at the C-(carboxyl)terminus thereof. The end-capping modification refers to the attachment of a chemical moiety to the terminus, so as to form a cap. Such a chemical moiety is referred to herein as an end-capping moiety and is typically also referred to herein and in the art, interchangeably, as a peptide protecting moiety or group.

The phrase "end-capping moiety", as used herein, refers to a moiety that when attached to the terminus of the peptide, modifies the end-capping. The end-capping modification typically results in masking the charge of the peptide terminus, and/or altering chemical features thereof, such as, hydrophobicity, hydrophilicity, reactivity, solubility and the like. Examples of moieties suitable for peptide end-capping modification can be found, for example, in Green et al., "Protective Groups in Organic Chemistry", (Wiley, second ed. 1991) and Harrison et al., "Compendium of Synthetic Organic Methods", Vols. 1-8 (John Wiley and Sons, 1971-1996).

The use of end-capping modification, allows to control the chemical properties and charge of the nanostructures, hence also the way the peptide nanostructures of the present embodiments are assembled and/or aligned.

Changing the charge of one or both termini of one or more of the peptides may result in altering the morphology of the resulting nanostructure and/or the way the resulting nanostructure responds to, for example, an electric and/or magnetic fields.

End-capping of a peptide can be used to modify its hydrophobic/hydrophilic nature. Altering the hydrophobic/hydrophilic property of a peptide may result, for example, in altering the morphology of the resulting nanostructure and/or the aqueous solubility thereof. By selecting the percentage of the end-capping modified peptides and the nature of the end capping modification, the hydrophobicity/hydrophilicity, as well as the solubility of the nanostructure can be finely controlled. For example, the end capping modification can be selected to control adherence of nanoparticles to the wall of the nanostructures.

While reducing the present invention to practice, the present inventors have uncovered that modifying the end-capping of a peptide does not abolish its capacity to self-assemble into nanostructures, similar to the nanostructures formed by unmodified peptides. The persistence of the end-capping modified peptides to form nanostructures supports the hypothesis of the present inventors according to which the dominating characteristic required to form peptides nanostructures is the aromaticity of its side-chains, and the π-stacking interactions induced thereby, as previously described in, for example WO 2004/052773 and WO 2004/060791, the contents of which are hereby incorporated by reference.

It was further found by the present inventors that the aromatic nature of at least one of the end-capping of the peptide affects the morphology of the resulting nanostructure. For example, it was found that an unmodified peptide or a peptide modified with a non-aromatic end-capping moiety can self-assemble to a tubular nanostructure.

Representative examples of N-terminus end-capping moieties suitable for the present embodiments include, but are not limited to, formyl, acetyl (also denoted herein as "Ac"), trifluoroacetyl, benzyl, benzyloxycarbonyl (also denoted herein as "Cbz"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitroveratryloxycarbonyl ("NVOC").

Representative examples of C-terminus end-capping moieties suitable for the present embodiments are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined herein.

In some embodiments of the present invention, all of the peptides that form the nanostructures are end-capping modified.

End-capping moieties can be further classified by their aromaticity. Thus, end-capping moieties can be aromatic or non-aromatic.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

Representative examples of aromatic end capping moieties suitable for N-terminus modification include, without limitation, fluorenylmethyloxycarbonyl (Fmoc). Representative examples of aromatic end capping moieties suitable for C-terminus modification include, without limitation, benzyl, benzyloxycarbonyl (Cbz), trityl and substituted trityl groups.

When the nanostructures of the present embodiments comprise one or more dipeptides, the dipeptides can be collectively represented by the following general Formula I:

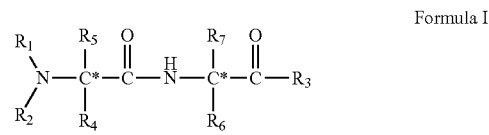

Formula I where:

C* is a chiral carbon having a D configuration or L configuration; $R_1$ and $R_2$ are each independently selected from the group consisting of hydrogen, alkyl, cycloalkyl, aryl, carboxy, thiocarboxy, C-carboxylate and C-thiocarboxylate; $R_3$ is selected from the group consisting of hydroxy, alkoxy, aryloxy, thiohydroxy, thioalkoxy, thioaryloxy, halo and amine; and each of $R_4$-$R_7$ is independently selected from the group consisting of hydrogen, alkyl, cycloalkyl, aryl, heteroaryl, heteroalicyclic, hydroxy, thiohydroxy (thiol), alkoxy, aryloxy, thioalkoxy, thioaryloxy, C-carboxylate, C-thiocarboxylate, N-carbamate, N-thiocarbamate, hydrazine, guanyl, and guanidine, as these terms are defined herein, provided that at least one of $R_4$-$R_7$ comprises an aromatic moiety, as defined hereinabove.

Also contemplated are embodiments in which one or more of $R_4$-$R_7$ is other substituent, provided that at least one comprises an aromatic moiety.

Also contemplated are embodiments in which one or more of $R_1$-$R_3$ is the end-capping moieties described hereinabove.

The peptide nanostructures of the present embodiments can further comprise a functional group, preferably a plurality of functional groups.

The functional group can be, for example, a group such as, but not limited to, thiol, hydroxy, halo, carboxylate, amine, amide, nitro, cyano, hydrazine, and the like, a hydrophobic moiety, such as, but not limited to, medium to high alkyls, cycloalkyls and aryls, and/or a metal ligand.

The nanostructure array of the present embodiments has chemical and mechanical stability. The ability to decorate the nanostructures of the present embodiments with functional groups enables their integration into many applications.

As stated, when the nano structures of the present embodiments have a tubular structure, it can be filled with a filler material.

For example, the nanostructures may enclose conducting or semiconducting materials, including, without limitation, inorganic structures such as Group IV, Group III/Group V, Group II/Group VI elements, transition group elements, or the like.

As used herein, the term "Group" is given its usual definition as understood by one of ordinary skill in the art. For instance, Group II elements include Zn, Cd and Hg; Group III elements include B, Al, Ga, In and Tl; Group IV elements include C, Si, Ge, Sn and Pb; Group V elements include N, P, As, Sb and Bi; and Group VI elements include O, S, Se, Te and Po.

Thus, for conducting materials, the nanostructures may enclose, for example, silver, gold, copper, platinum, nickel, or palladium. For semiconducting materials the nanostructures may enclose, for example, silicon, indium phosphide, gallium nitride and others.

The nanostructures may also encapsulate, for example, any organic or inorganic molecules that are polarizable or have multiple charge states. For example, the nanostructures may include main group and metal atom-based wire-like silicon, transition metal-containing wires, gallium arsenide, gallium nitride, indium phosphide, germanium, or cadmium selenide structures.

Additionally, the nanostructure of the present invention may enclose various combinations of materials, including semiconductors and dopants. Representative examples include, without limitations, silicon, germanium, tin, selenium, tellurium, boron, diamond, or phosphorous. The dopant may also be a solid solution of various elemental semiconductors, for example, a mixture of boron and carbon, a mixture of boron and P, a mixture of boron and silicon, a mixture of silicon and carbon, a mixture of silicon and germanium, a mixture of silicon and tin, or a mixture of germanium and tin. In some embodiments, the dopant or the semiconductor may include mixtures of different groups, such as, but not limited to, a mixture of a Group III and a Group V element, a mixture of Group III and Group V elements, a mixture of Group II and Group VI semiconductors. Additionally, alloys of different groups of semiconductors may also be possible, for example, a combination of a Group II-Group VI and a Group III-Group V semiconductor and a Group I and a Group VII semiconductor.

Specific and representative examples of semiconducting materials which can be encapsulated by the nanostructure of the present invention include, without limitation, CdS, CdSe, ZnS and $SiO_2$.

The nanostructure of the present invention may also enclose a thermoelectric material that exhibits a predetermined thermoelectric power. Preferably, such a material is selected so that the resulting nanostructure composition is characterized by a sufficient figure of merit. Such composition, as further detailed hereinunder, may be used in thermoelectric systems and devices as heat transfer media or thermoelectric power sources. According to a preferred embodiment of the present invention the thermoelectric material which can be encapsulated in the nanostructure of the present invention may be a bismuth-based material, such as, but not limited to, elemental bismuth, a bismuth alloy or a bismuth intermetallic compound. The thermoelectric material may also be a mixture of any of the above materials or other materials known to have thermoelectric properties. In addition the thermoelectric material may also include a dopant. Representative examples include, without limitation, bismuth telluride, bismuth selenide, bismuth antimony telluride, bismuth selenium telluride and the like. Other materials are disclosed, for example, in U.S. Patent Application No. 20020170590.

The nanostructure of the present invention may also enclose magnetic materials. Generally, all materials in nature posses some kind of magnetic properties which are manifested by a force acting on a specific material when present in a magnetic field. These magnetic properties, which originate from the sub-atomic structure of the material, are different from one substrate to another. The direction as well as the magnitude of the magnetic force is different for different materials.

Whereas the direction of the force depends only on the internal structure of the material, the magnitude depends both on the internal structure as well as on the size (mass) of the material. The internal structure of the materials in nature, to which the magnetic characteristics of matter are related, is classified according to one of three major groups: diamagnetic, paramagnetic and ferromagnetic materials, where the strongest magnetic force acts on ferromagnetic materials.

In terms of direction, the magnetic force acting on a diamagnetic material is in opposite direction than that of the magnetic force acting on a paramagnetic or a ferromagnetic material. When placed in external magnetic field, a specific material acquires a non-zero magnetic moment per unit volume, also known as a magnetization, which is proportional to the magnetic field vector. For a sufficiently strong external magnetic field, a ferromagnetic material, due to intrinsic non-local ordering of the spins in the material, may retain its magnetization, hence to become a permanent magnet. As opposed to ferromagnetic materials, both diamagnetic and paramagnetic materials loose the magnetization once the external magnetic field is switched off.

Representative examples of paramagnetic materials which can be enclosed by the nanostructure of the present invention include, without limitation, cobalt, copper, nickel, and platinum. Representative examples of ferromagnetic materials include, without limitation, magnetite and NdFeB.

Other materials which may be encapsulated by the nanostructure of the present invention include, without limitation, light-emitting materials (e.g., dysprosium, europium, terbium, ruthenium, thulium, neodymium, erbium, ytterbium or any organic complex thereof), biominerals (e.g., calcium carbonate) and polymers (e.g., polyethylene, polystyrene, polyvinyl chloride, polynucleotides and polypeptides).

Following is a description of various applications which incorporate the nanostructure array of the present embodiments.

The type of nanostructures in the array is preferably selected according to the application for which the array is designated. For example, in applications in which the nanostructure array serves for conducting electrical current (e.g., when the nanostructure array is an electrode), the nanostructures of the nanostructure array are filled or coated by a conductive material, as described above; in applications in which the nanostructure array serves for conducting heat, the nanostructures of the nanostructure array are filled or coated by a heat conducting material, such as a metal; in applications in which the nanostructure array serves as a semiconductor channel, the nanostructures of the nanostructure array are filled or coated by a semiconductor material, as described above; and in applications in which the nanostructure array functions as a magnetic object, the nanostructures of the nanostructure array are filled or coated by a magnetic material, as described above.

When the nanostructure array comprises a substrate, the type, shape and material of the substrate is selected according to the application for which the array is designated. Thus, the substrate can be made of or coated by a dielectric material, a conductive material, a heat a conductive material, a semiconductor material and the like.

Generally, the nanostructure array of the present invention can be used in various applications which involve the use of nanoscopic elements. Such applications are disclosed in U.S. Pat. Nos. 5,581,091, 6,383,923, 6,428,811, 6,504,292, 6,559,468, 6,579,742, 6,586,095, 6,628,053, 7,163,659 and in U.S. Patent Application Nos. 20020053257, 20020054461, 20020175618, 20020187504, 20030089899, 20030121764, 20030141189, 20030165074, and 20030197120, the contents of which are hereby incorporated by reference.

In some embodiments of the present invention the nanostructure array of the present embodiments can be used in a field effect transistor (FET), whereby the nanostructure array can serve, e.g., as a channel interconnecting a source and a drain. Of particular advantage is the embodiment in which a plurality of nanostructures is aligned vertically to the other electrodes of the FET.

Figure 2:
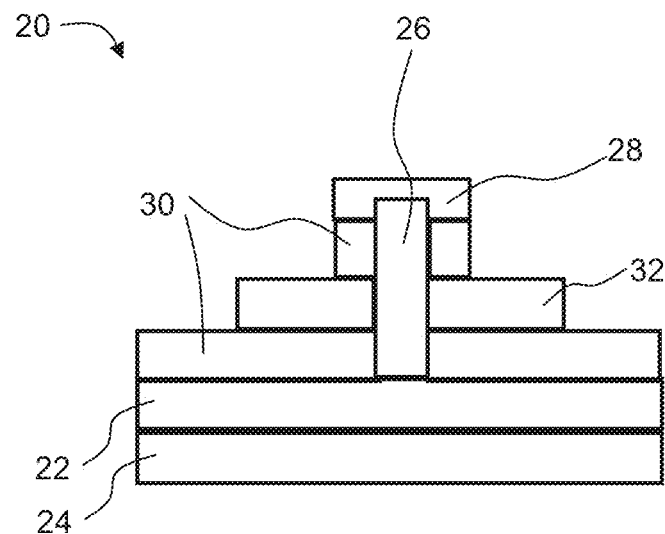

FIG. 2 is a schematic cross-sectional illustration of a transistor 20 according to an embodiment of the present invention. Transistor 20 comprises a first electrode 22 acting as a drain formed on a substrate 24, an array 26 of nanostructures acting as a channel and a second electrode 28 acting as a source formed on array 26. Array 26 is aligned vertically with respect to first electrode 22. Array 26 can be any of the arrays described above.

One portion of array 26 is enclosed by a gate 32, while the remaining portion is shielded by buried layers 30 acting as spacers made of an insulating material to protect and support array 26. Due to the structure in which gate 32 completely encloses the channel (array 26), the effect of an electric field around the channel is maximized and a fully depleted depletion layer is obtained by an electric field produced by gate 32, thereby maximizing a ratio on/off.

The nanostructure array of the present embodiments can also serve as a conductive layer for multiple conductors in an integrated circuit chip.

Figure 3:
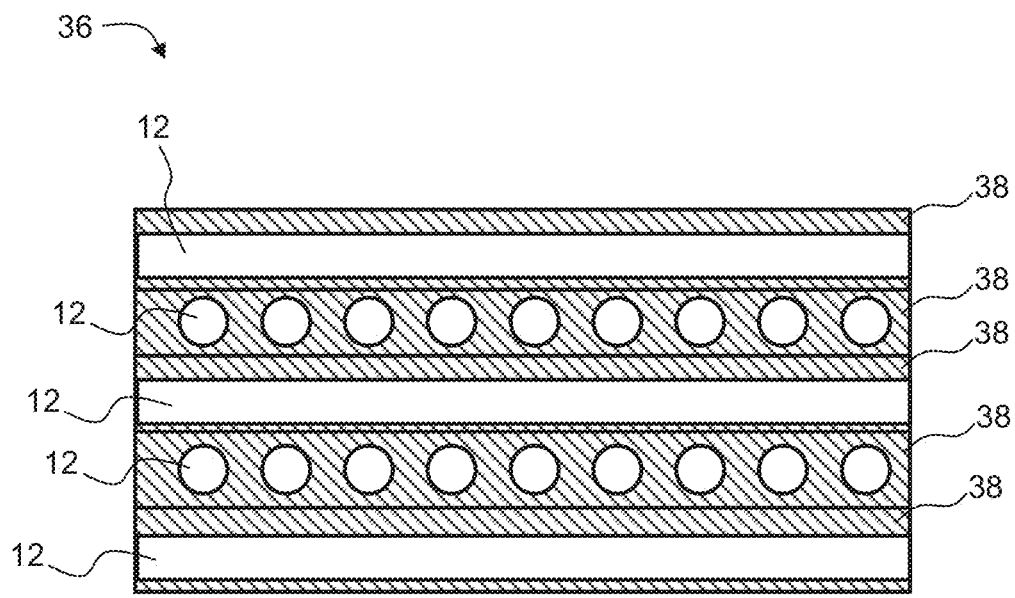

FIG. 3 is a schematic illustration of a cross sectional view of conductive layer 36, according to various exemplary embodiments of the present invention. Conductive layer 36 can be constructed, for example, as a stack of multiple sublayers 38 (five such sublayers are shown in FIG. 3) in which one or more sublayers comprise oriented nanostructures, such as nanostructures 12. Different sublayers can include nanostructures which are oriented to different directions. For example, all the nanostructures in one sublayer can be aligned substantially parallel to each other in a first direction, and all the nanostructures in another sublayer (e.g., an adjacent sublayer) can be aligned substantially parallel to each other in a second direction, e.g., perpendicular to the first direction. Because the nanostructures of the present embodiments can have an extremely high conductivity and current carrying capacity, they can carry the bulk of the electrical current within the conductors of the conductive layer. Since the nanostructures are elongated, their conductivity is non-isotropic and is primarily along the longitudinal direction of the nanostructures. By arranging multiple sublayers of the nanostructures of the present embodiments in different direction, high conductivity can be achieved in any direction in the plane of the conductive layers.

The nanostructure array of the present embodiments can also be incorporated in sensing and/or stimulating devices, for example, a medical lead. This embodiment is particularly useful when the nanostructures are vertically aligned. Such medical lead can have improved electrode performance due to the high surface area of the nanostructure array. The medical lead can be used for cardiac pacing and/or sensing, brain stimulations and/or sensing and the like.

Figure 4A:
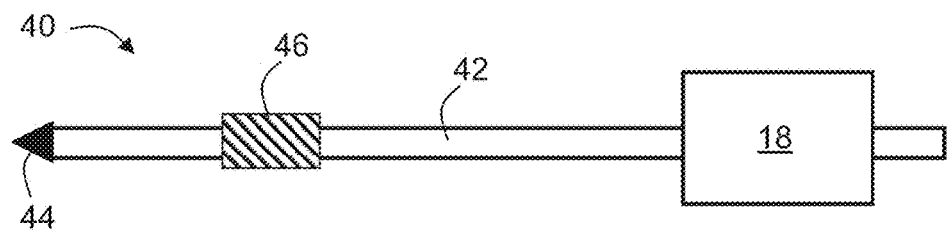
Figure 4B:
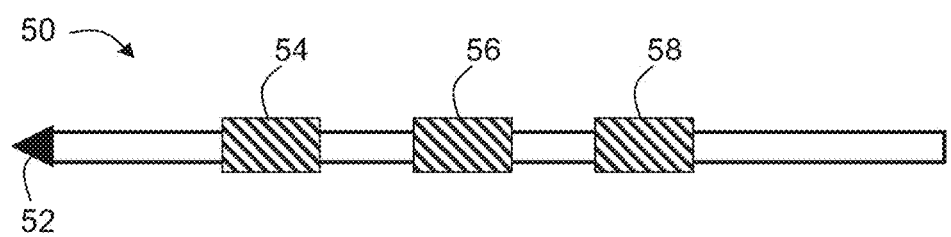

FIGS. 4a-b are schematic illustrations of medical leads, according to various exemplary embodiments of the present invention.

FIG. 4a illustrates a medical lead 40 that may typically be used for cardiac pacing and/or sensing. Lead 40 is provided with an elongated lead body 42, a tip electrode 44 located at the distal end of the lead and a ring electrode 46 spaced proximally from tip electrode 44. A connector assembly 48 at the proximal end of lead 40 is used to connect the lead to a medical device, such as a pacemaker. Conductors extending the length of lead body 42 electrically couple tip electrode 44 and ring electrode 46 to respective connectors carried by the connector assembly 48. At least one of electrodes 44 and 46 can comprise a nanostructure array as further detailed hereinabove. Preferably, one of more of electrodes 44 and 46 comprises the "forest" nanostructure described above.

FIG. 4b schematically illustrates a distal end of a medical lead 50 of the type that may be used for pacing, sensing, cardioversion and/or defibrillation. Lead 50 is provided with a tip electrode 52 and a ring electrode 54, which are generally used for pacing and/or sensing, and two defibrillation coil electrodes 56 and 58 for delivering high-energy shocking pulses for cardioversion or, defibrillation. At least one of electrodes 52 and 54 can comprise a nanostructure array as further detailed hereinabove. Preferably, one of more of electrodes 52 and 54 comprises the "forest" nanostructure described above.

The exemplary leads 40 and 50 are shown to illustrate the various types of electrodes, including ring electrodes, coil electrodes, tip electrodes, which can be comprise the nanostructure array of the present embodiments. Other electrodes of various geometries may exist that may also benefit from the use of the nanostructure assembly. The present embodiments may also be used in conjunction with electrodes for neurological stimulation or sensing, smooth or skeletal muscle sensing or stimulation or any other types of medical electrodes that may benefit from increased active surface area and/or increased current density capacity.

The nanostructure array of the present embodiments can also used for transporting thermal energy to or from an object.

FIG. 5 schematically illustrates a device 60 for transporting thermal energy to or from an object 66, according to various exemplary embodiments of the present invention. An array of nanostructures such as, but not limited to, nanostructures 12 is grown or otherwise provided on a selected surface of a substrate 64 having an optional catalyst layer 62. A layer of filler material 68, having a depth that allows exposure of an upper portion of each nanostructure, can be provided, for mechanical strengthening of the nanostructures and for improved diffusion of heat that initially travels only along the nanostructures. The nanostructures can be pressed against a surface of object 66, from which heat is to be removed (or to which heat is to be delivered)

such that many or, more preferably, all of the nanostructures make contact with the object surface, which is typically rough. As a results, the pressed nanostructures can be bend or buckle hence further improving heat transport between object 66 and nanostructures 12. Nanostructures 12 and optionally substrate 64 can be exposed to the environment so as to evacuate heat to the environment. Thus, the nanostructure array of the present embodiments can serve as a heat sink.

The nanostructure array of the present embodiments can also be used in various sensors, include, without limitation, electrochemical sensors, mechanical sensors, electromechanical sensors and the like.

FIG. 6 is a schematic illustration of a sensor system 70 according to various exemplary embodiments of the present invention. Sensor system 70 can comprise a substrate 72 with spaced-apart electrodes 74 and 76 positioned on substrate 72 such that portions thereof oppose one another with a gap 78 being defined therebetween. Electrodes 74 and 76 can be, but are not required to be, parallel to one another as is the case in the illustrated example. A plurality of nanostructures such as, but not limited to, nanostructures 12 described above are operatively positioned on substrate 72. Each nanostructure spans gap 78 between opposing portions of electrodes 74 and 76. The opposing ends of each nanostructure are in electrical contact with a respective one of electrodes 74 and 76.

Sensor system 70 can be used to monitor strain, pressure, or temperature changes experienced by a structure to which the sensor system is coupled. The structure can be dynamic in nature (e.g., air, space, water, or land craft) or static in nature (e.g., building, bridge, etc.). Typically, substrate 72 is coupled to a portion of a structure that is to be monitored with the sensor system being capable of monitoring changes at that portion of the structure. Substrate 72 may be part of the structure itself provided the nanostructures can be deposited thereon.

The sensor system of the present embodiments can be optimized to monitor specific types of change. For example, if changes in a structure's strain experience are of concern, substrate 72 can be made from a flexible material such as a polymer or an elastomer. If the sensor system is to be optimized for monitoring pressure and/or temperature changes, substrate 72 can be made from an inflexible material. If the sensor system is to be optimized for temperature alone, substrate 72 can be made from an inflexible material and the nanostructure portion of the system can be coated with a rigid, air-impermeable membrane to eliminate pressure sensitivity A sensor incorporating the nanostructure array of the present embodiments can also operate according to the principles of quartz crystal microbalance (QCM) sensors for the detection and measurements of low-mass objects, e.g., bacteria or the like. Thus, the nanostructures can be aligned such that at least one tube is exposed to the object and at least one tube is not exposed to the object. The difference in resonance frequencies between the exposed and isolated nanostructure array is indicative of the mass of the object of interest.

Due to its large surface area, the nanostructure array of the present embodiments can also be used for collecting analytes from a fluidic medium (gas or liquid), and for concentrating the analytes, e.g., for spectroscopy (e.g. Fourier transform spectroscopy, Fourier transform infrared spectroscopy, etc.)

In some embodiments of the present invention the nanostructure array is incorporated in a biosensor device. Such device can comprise a substrate which is responsive to an electrochemical signal and a nanostructure array which is preferably generally perpendicular to the substrate. The device can also include a capture antibody or an enzyme attached to one or more of the nanostructures in the area.

Substrates responsive to an electrochemical signal which are suitable for the present embodiments include electrical conductors that conduct a current in and out of an electrically conducting medium. The electrical conductor may be present in the form of an array, consisting of a number of separately addressable electrical conductors. The electrical conductor can be made of gold, copper, carbon, tin, silver, platinum, palladium, indium tin oxide or combinations comprising one or more of the foregoing materials. In one embodiment, the electrical conductor is in the form of a layer.

The nanostructures of the present embodiments greatly increase the surface area of traditional 2-D biosensors while providing surface functional groups for bioconjugation with bioactive molecules such as enzymes and capture antibodies. A variety of bioconjugation techniques may be employed, including adsorption and covalent bonding.

Suitable bioactive molecules for use in the biosensor of the present embodiments include enzymes that participate in electrochemical reduction pathways such as those involving peroxides. Suitable capture antibodies for use in the biosensor of the present embodiments are those that are useful for the immunological detection of an antigen of interest.

In use, the biosensor is contacted with a test sample under conditions suitable for binding of the analyte to the capture antibody. The contacting generates, directly or indirectly, a signal which can then be detected. The detection is preferably performed by electrochemical means.

It is expected that during the life of a patent maturing from this application many relevant sensor systems will be developed and the scope of the term "sensor" is intended to include all such new technologies a priori.

Following is a description of a method for a method suitable for fabricating a nanostructure array, according to various exemplary embodiments of the present invention.

In some embodiments of the present embodiments organic monomers dissolved in an organic volatile solvent are dispensed or placed on a substrate. The organic monomers can be peptide monomers as further detailed hereinabove. The solvent is preferably selected so as to allow dispersion of the organic monomers in the solution prior to evaporation of the solvent. The concentration of the organic monomers in the solvent depends on the type of the organic monomers and substrate. In various exemplary embodiments of the invention the concentration is selected so as to allow self assembling of the organic monomers generally perpendicular to the substrate. In some embodiments the organic monomers concentration is at least 10 mg/ml, more preferably at least 20 mg/ml, more preferably at least 30 mg/ml, more preferably at least 40 mg/ml, more preferably at least 50 mg/ml. These embodiments are particularly, but not exclusively, suitable when the organic monomers are peptide monomers.

The substrate can be of any type or material. In various exemplary embodiments of the invention the substrate is planar. The substrate can be made of a dielectric, conductive or semiconductor material. Representative examples of substrate materials, include, without limitation, glass, silicon, silicon dioxide, siliconized glass, gold and indium tin oxide. Other materials are not excluded from the scope of the present invention.

While generating conditions for self assembling of said organic monomers, the solvent is evaporated such as to form a plurality of elongated organic nanostructures arranged generally perpendicularly on the substrate.

In some embodiments of the present embodiments the organic monomers are electrically charged. The charge of the monomer is preferably selected to establish repulsion forces between the monomers and to facilitate the orientation of the nanostructures. The monomers and/or substrate are preferably selected to establish repulsion forces between the monomers and the substrate hence to facilitate a generally vertical build-up of the nanostructures on the substrate. Once the nanostructures are formed on the substrate, they can be harvested off the substrate, to form an array of nanostructures which is generally perpendicular to a plane and which is devoid of any substrate attached thereto.

In some embodiments of the present invention, organic monomers and nanoparticles being responsive to a force field are incubated. The nanoparticles are typically inorganic and can be magnetic nanoparticles, in which case the force field is preferably a magnetic field, or electrically charged nanoparticles in which case the force field is preferably an electric field. The incubation condition is selected to allow self assembling of the organic monomers to elongated organic nanostructures and self coating of the elongated organic nanostructures by the nanoparticles. Thus, elongated nanostructures coated by one or more layers of nanoparticles are formed. During or subsequently to incubation, the force field is applied to the coated nanostructures such as to align the nanostructures generally parallel to each other. Optionally, the force field is directed generally parallel to the surface, such that the nanostructure assembly is aligned parallel to the surface. Once the nanostructures are aligned, they can be lifted off the substrate, to form a planar array of nanostructures devoid of any substrate attached thereto.

When the nanostructures of the present embodiments are filled with a filler material or coated with a coating material, the filling and/or coating can be done once the nanostructures are formed.

Filler material can be introduced into the internal cavity of the nanostructures to encapsulate the material in the nanostructure, using any technique known in the art, such as, but not limited to, electroless deposition and/or any of the techniques disclosed and/or referenced by International Patent Application, Publication No. WO2004/060791 and U.S. Pat. Nos. 5,916,642 and 6,361,861, the contents of which are hereby incorporated by reference.

The nanostructures can be coated by a coating material using any technique known in the art, such as, but not limited to, electroless deposition and/or any of the techniques disclosed and/or referenced by International Patent Application, Publication Nos. WO200106257, WO200228552 and WO2004052773 the contents of which are hereby incorporated by reference.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Vertically Aligned Aromatic Dipeptide Nanostructures

The formation of an array of vertically aligned aromatic dipeptide nanostructures is exemplified below.

Materials

Diphenylalanine and diphenylalanine peptide analogues were purchased from Bachem (Bubendorf, Switzerland). Fresh solutions of the diphenylalanine peptide and analogues were prepared by dissolving the lyophilized form of the peptides in 1,1,1,3,3,3-hexafluoro-2-propanol (HFP, Sigma). To avoid any pre-aggregation, fresh stock solutions were prepared for each experiment.

The following diphenylalanine peptide analogues were examined: (a) Ac-Phe-Phe-NH$_2$. (b) t-Butyl carbamate-Phe-Phe-COOH (Boc-Phe-Phe-COOH) (c) Carbobenzyloxy- Phe-Phe-COOH (Cbz-Phe-Phe-COoH) (d) Fluorenyl-methoxycarbonyl-Phe-Phe-COOH (Fmoc-Phe-Phe-COOH) (e) Cyclo-Phe-Phe.

Methods

The following peptide concentrations are presented in the Results section (see FIG. 12): 20 mg/ml, 40 mg/ml, 60 mg/ml, 80 mg/ml, 120 mg/ml and 180 mg/ml.

Figure 7A:
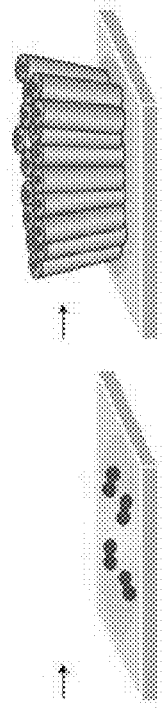
Figure 7A:
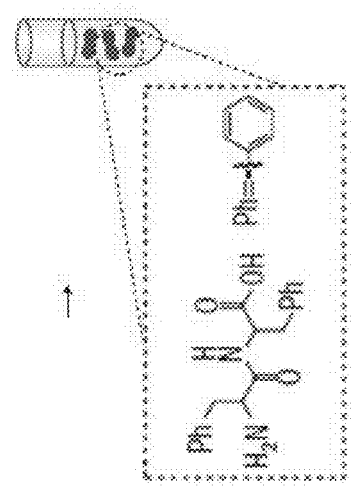
Figure 7A:
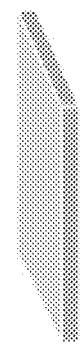

After dissolving the peptide in HFP to a final concentration of 100 mg/ml, a 30 μl of the solution was placed on a 22 mm in diameter siliconized glass (Hampton research, CA, USA), as illustrated in FIG. 7a. The highly volatile fluorinated alcohol is a remarkable solvent that allows the existence of the peptide entities as monodispersed building blocks. Upon the rapid evaporation of the HFP, a thin layer of vertically aligned peptide nanostructures was formed onto the substrate.

The layer was analyzed using scanning electron microscope (SEM). Samples were coated with gold and analyzed using JSM JEOL 6300 scanning electron microscopy (SEM) operating at 5 kV. For analysis by Cold field emission gun (CFEG) high-resolution scanning electron microscopy (HR-SEM), the samples were coated with Cr and viewed using a JSM-6700 field emission scanning electron microscope equipped with a cold field emission gun operating at 1 kV.

To determine the structure of the formed array, X-ray diffraction analysis (FIG. 7e) was performed. The X-ray diffraction measurements were made using a Ttrax theta-theta diffractometer (Rigaku, Japan) with copper anode, parallel beam optics and generator power of 12 kW.

Additionally, electron diffraction experiments were performed. Electron diffraction experiments were performed on an FEI Tecnai F20 microscope at 200 kV with a field-emission gun. Low-dose methods were used; searching was performed at extremely low doses and low magnification, and then electron diffraction patterns were recorded directly to the camera; a TVIPS F415 camera with 4 k×4 k pixels, with a 500 ms exposure time. Electron diffraction analysis of individual tube was consistent with a unit cell of a=~21.0 Å, b=5.4 Å, where a is oriented normal to the long axis of the crystal. In studies of three different tubes, b was always 5.4 Å, where a varied between 20.5 Å and 21.9 Å. This is consistent with the unit cell of [a=24.1 Å, b=24.1 Å, c=5.5 Å] as was determined for the single crystal of diphenylalanine.

To further explore the role of electrical charge in this process, the assembly of the diphenylalanine peptide on a surface in its deprotonated state was studied by the addition of N,N-diisopropylethylamine (DIAE) to the dissolved peptide monomers. Images were obtained images for the following DIAE concentrations: 0.5% DIAE, 1% DIAE, 2% DIAE and 5% DIAE.

Results

Figure 7D:
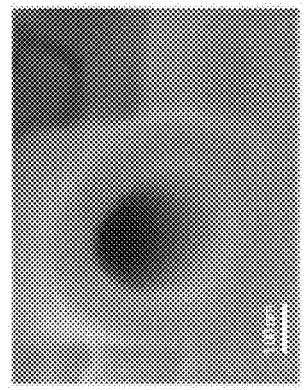
Figure 7C:
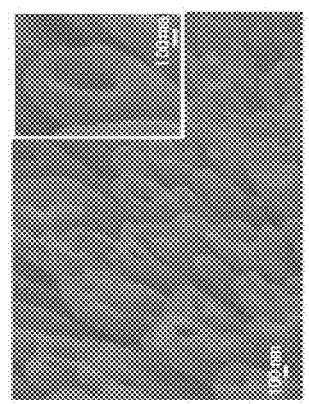
Figure 7B:
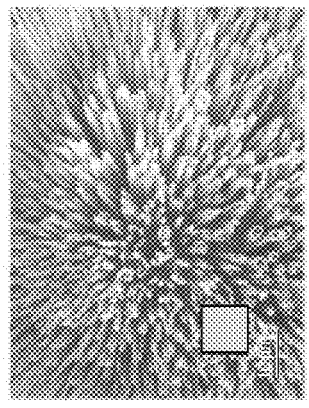
Figure 7E:
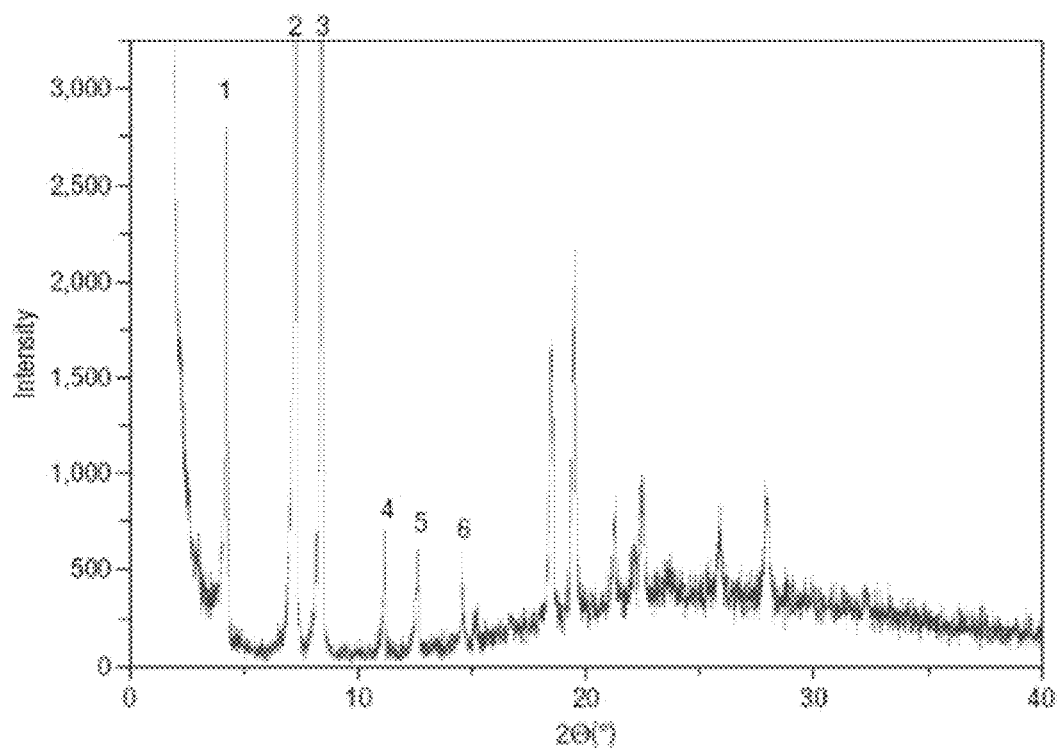

SEM analysis of the thin layer formed on the substrate revealed that a vertically aligned array of peptide nanostructures was formed (FIG. 7b). The peptide nanostructures in this experiment had a tubular shape and are referred to in this example as peptide nanotubes.

Analysis by high-resolution SEM provided an insight into the ordered array of tubes and revealed their structural open-end conformation (FIG. 7c). In addition, the multi-walled structure of the tubes was clearly observed, since their outer diameter is much wider than their interior cavity (FIG. 7d).

Without being bound to any theory, it is assumed that the ordered organization of the structures is facilitated by the geometrically restricted stacking of the aromatic moieties in the direction of the growth axis derived by the vapor-liquid-solid system that exists during the rapid evaporation of the HFP solvent. Referring to FIG. 11, the peptide building blocks are being deposited as monomers in HFP solution. The rapid evaporation leads to supersaturation and crystallization process. The differential growth rates at the different directions lead to the formation of elongated sheets. The two dimensional elongated sheets tend to form close tubular structures.

Figure 7F:
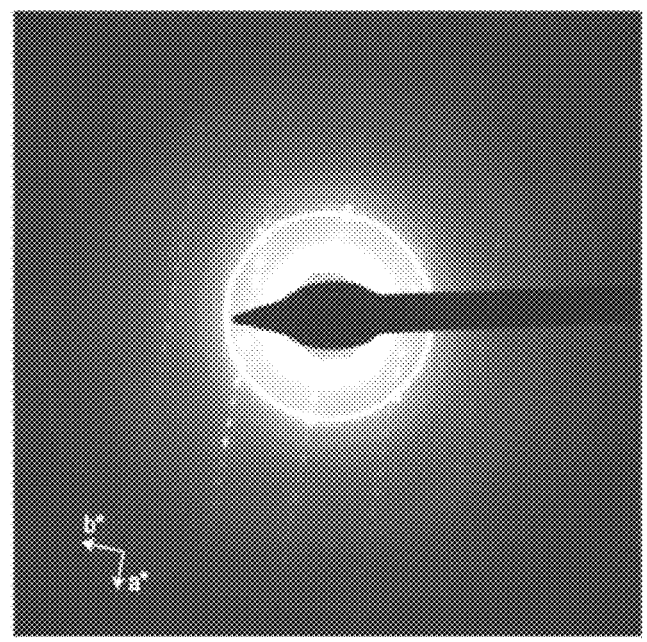

To determine the structure of the formed array array, X-ray diffraction analysis (FIG. 7e) was performed. The 6-fold symmetry observed is very similar to the one that was found with a single crystal of diphenylalanine or the powder diffraction under conditions that lead to the formation of nanotubes in solution [26-27]. As these experiments were performed on a crystal or a large collection of nanotubes, the electron diffraction pattern of an individual nanotube was determined (FIG. 7f). The result suggests that the conclusions drawn for tube collection are also valid on the single tube level. The level of the nanotubes' ordering was observed by tilting experiments in which the angle of the sample was changed at the High-resolution scanning electron microscope (HR-SEM) chamber (FIG. 8).

Without being bound to any theory, it is suggested that the rapid evaporation of the HFP solvent results in a super-saturation state that facilitates the formation of numerous nucleation sites on the surface. This is followed by a unidirectional growth of the nanotubes as more diphenylalanine monomers are stacked on the nucleation sites and sediment away on the surface toward the liquid-air interface. The process of assembly was observed using light microscopy. While the peptide solution is completely clear for a few seconds following the deposition, a simultaneous and coordinated formation of ordered structures occurs as soon as evaporation is allowed. Each nucleation event results in the formation of a vertical array of nanotubes across an area of 100 μm$^2$ and the coverage of the whole surface with these ordered structures (FIG. 7b). Other mechanisms of assembly are also contemplated. For example, solution-initiated assembly can be followed by organization of the pre-formed tubes into a vertical array of nanotubes.

Alignment of the peptide building blocks was observed in peptide concentrations ranging from 160 mg/ml to 60 mg/ml. FIGS. 12a-12f, are SEM images for the peptide concentrations: (a) 20 mg/ml. (b) 40 mg/ml. (c) 60 mg/ml. (d) 80 mg/ml. (e) 120 mg/ml. (f) 180 mg/ml.

Figure 12A:
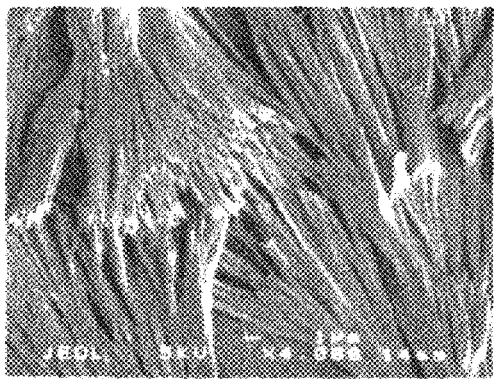
Figure 12B:
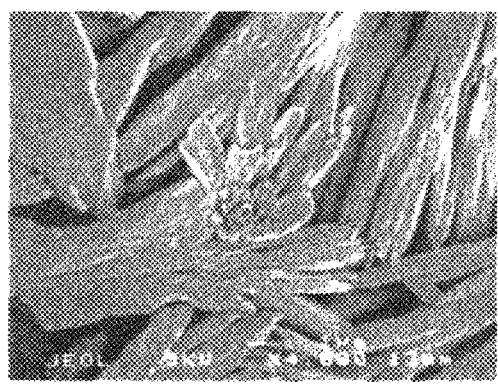
Figure 12C:
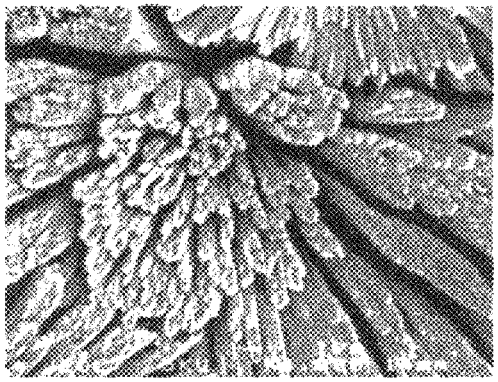
Figure 12D:
Figure 12E:
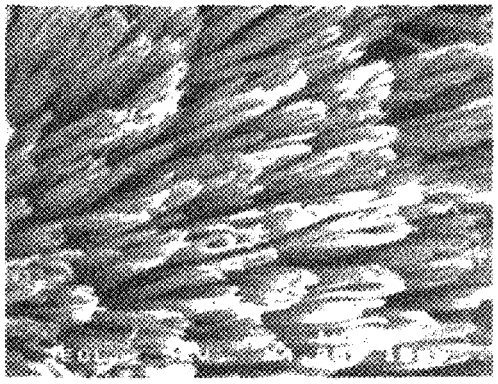
Figure 12F:
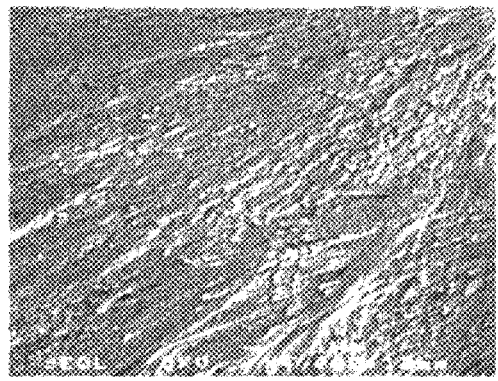
Figure 13A:
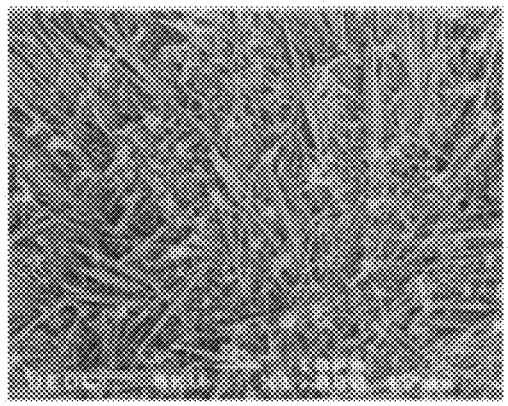
Figure 13D:
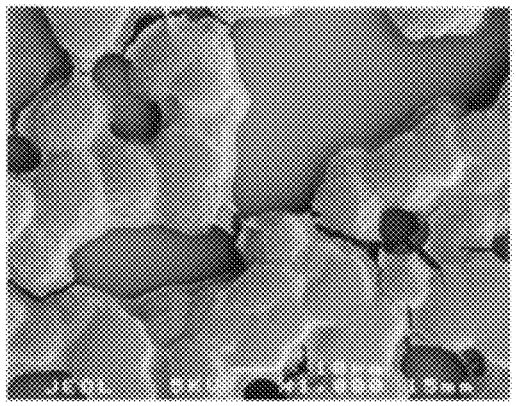
Figure 13B:
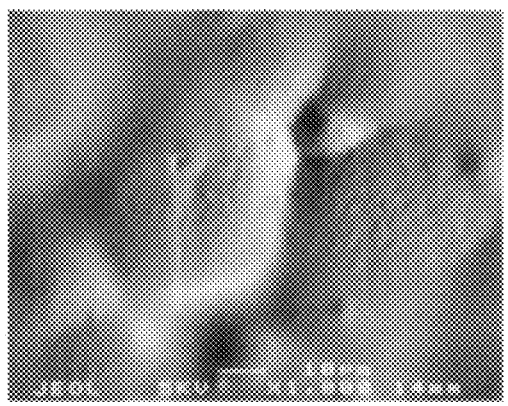
Figure 13E:
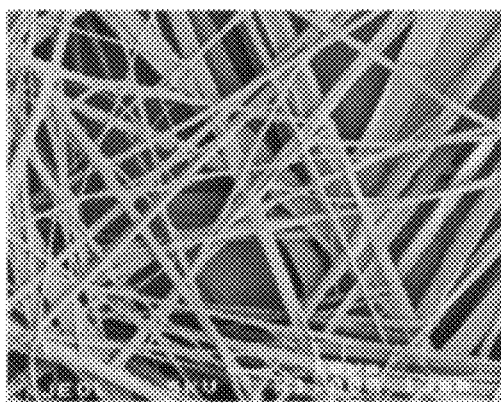
Figure 13C:
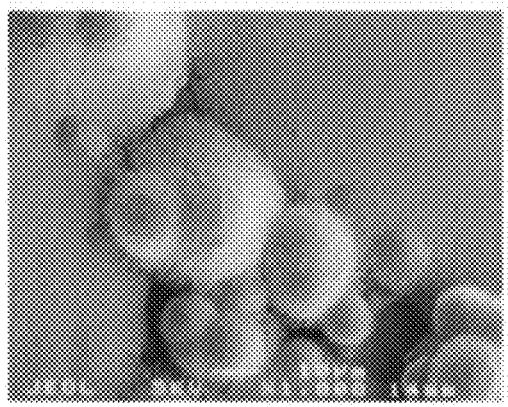
Figure 14A:
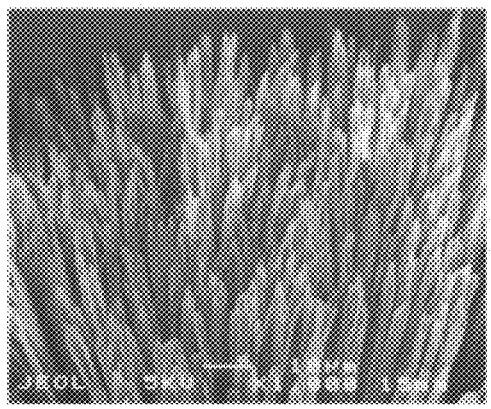
Figure 14B:
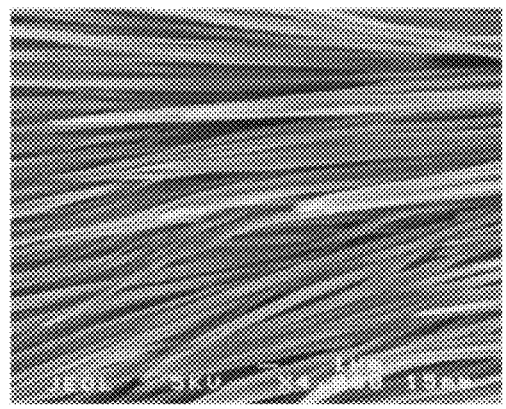
Figure 14C:
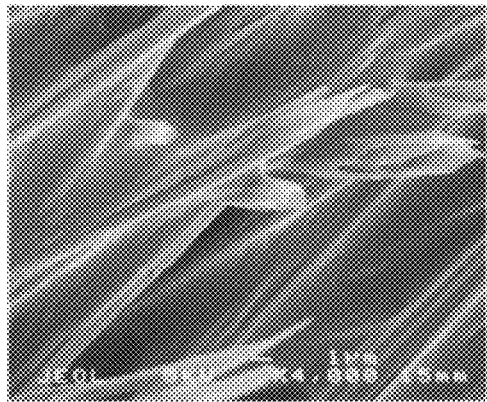
Figure 14D:
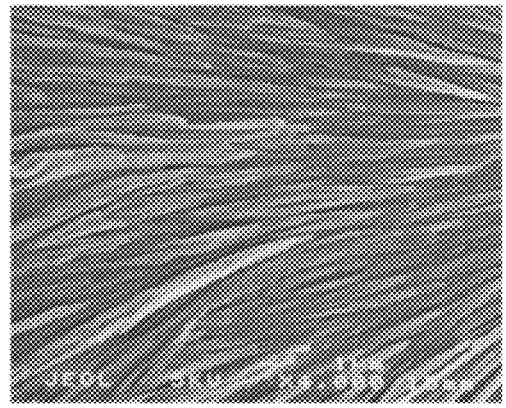

At lower concentrations, nanotubes formation was detected but with no specific orientation (FIGS. 12a,b). It is assumed that the lower concentration limit reflects the inability of the peptide monomer used in the present experiment to nucleate with super-saturation driven growth at the surface used in the present experiment. It is also assumed that the higher concentration limit results from the uncontrolled growth of the monomers used in the present experiment along multiple axes (FIG. 12f). Yet, other concentrations may be used with other organic monomers and other substrates.

The assembly of the peptide monomers into ordered nanostructures upon the allowed evaporation, as reflected by the diffraction experiment, may be the result of a preferred crystallization process. The concentration of the building blocks upon evaporation results in the transition of the solution into the labile phase. In the case of aggregation into amorphous clusters, no phase transition and phase separation are observed. These findings further support a nucleation-driven mechanism of formation.

To resolve the molecular basis for the vertical self-organization, the self-assembly of various diphenylalanine analogues was monitored FIGS. 9a-c demonstrate that positively charged diphenylalanine peptide analogue, can self assemble onto siliconized glass in the same manner as the diphenylalanine peptide. These analogues are able to form nano-assemblies by self-association in aqueous solution, yet they differ from the original diphenylalanine in their electrostatic charge state. Note that the native peptide is zwitterionic under neutral conditions with a positively charged amine group and a negatively-charged carboxyl group.

Table 1 below presents the chemical structure of the diphenylalanine peptide analogues used in the present Example. At neutral pH, these compounds exist in a range of charge states. The parent diphenylalanine ($NH_2$-Phe-Phe-COOH) is zwitterionic and bears a positively charged ammonium group and a negatively charged carboxylate group. The N-acetylated (Ac5acetyl) compound (Ac-Phe-Phe-$NH_2$) is neutral and carries no charge. The amide derivative of diphenylalanine ($NH_2$-Phe-Phe-$NH_2$) carries a single positive charge, whereas the final three entries each carry a single negative charge, but differ in the nature of the group attached to the N-terminus of the dipeptide, namely t-butoxycarbonyl (Boc), fluorenylmethoxycarbonyl (Fmoc) or benzyloxycarbonyl (Cbz).

SEM analysis of these analogues revealed that electrical charge effects the self-assembly process; while a non-charged analogue, Ac-Phe-Phe-$NH_2$, formed non-oriented tubular structures on the surface (FIG. 13), a positively charged peptide, $NH_2$-Phe-Phe-$NH_2$, formed an aligned structures upon this deposition process (FIG. 9).

A t-Butyl carbamate-Phe-Phe-COOH (Boc-Phe-Phe-COOH) peptide was used to explore the role of negative charge in this process. This peptide did not form aligned tubular structure as the positively charged analogue. This was also the case with other negatively charged peptide analogues that were modified with larger moieties. A cyclic analogue, which has no net charge, assembled into well-ordered tubular structures with a random orientation on the surface (FIG. 13). It is suggested that this random assembly on the surface results from the lack of repulsion forces to facilitate the tubes orientation. In the case of the negatively charged peptides, tubular structures could not be detected in the same manner as in solution due to their interaction with the surface.

To further explore the role of electrical charge in this process, the assembly of the diphenylalanine peptide on a surface in its deprotonate state was studied by the addition of N,N-diisopropylethylamine (DIAE) to the dissolved peptide monomers.

FIGS. 14a-d are the obtained images for (a) 0.5% DIAE, (b) 1% DIAE, (c) 2% DIAE, and (d) 5% DIAE. In the presence of 0.5% DIAE, aligned tubular structures were formed, however when DIAE concentration was increased the order and directionality of the tubes was affected and random orientation was observed (FIG. 14). It is assumed that dipeptide discharge due to the high concentrations of the base affects the directionality of the assembling process. When applied onto a positively charged surface, the diphenylalanine peptide did not self-assemble into an aligned array. These experimental results further suggest that extremely ordered but discrete peptide arrays are being stabilized by repulsive electrostatic interactions between the self-assembled nanostructures.

TABLE 1

| Peptide Name | Molecular Structure |
| --- | --- |
| $NH_2$—Phe-Phe—COOH | 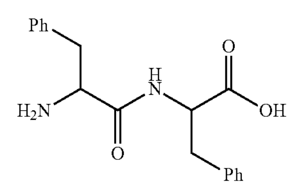 [SMILES: NC(Cc1ccccc1)C(=O)NC(Cc1ccccc1)C(=O)O] |
| Ac—Phe-Phe—$NH_2$ | 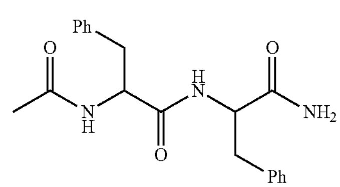 [SMILES: CC(=O)NC(Cc1ccccc1)C(=O)NC(Cc1ccccc1)C(N)=O] |
| $NH_2$—Phe-Phe—$NH_2$ | 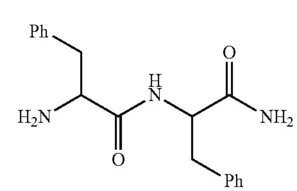 [SMILES: NC(=O)C(Cc1ccccc1)NC(=O)C(N)Cc1ccccc1] |

TABLE 1-continued

| Peptide Name | Molecular Structure |
|---|---|
| Boc—Phe-Phe—COOH | *(structure shown)* |
| Fmoc—Phe-Phe—COOH | *(structure shown)* |
| Cbz—Phe-Phe—COOH | *(structure shown)* |

Example 2

Horizontally Aligned Aromatic Dipeptide Nanostructures

The present Inventors successfully employed the method of the present embodiments to form an array of horizontally aligned aromatic dipeptide nanostructures. To form the array a magnetic field was applied. Although the use of a magnetic field to align carbon nanotubes and inorganic nanoparticles is widely studied [30], the use of magnetic field with organic nanostructures presents a major challenge.

Materials

Diphenylalanine and diphenylalanine peptide analogues were purchased from Bachem (Bubendorf, Switzerland). Fresh solutions of the diphenylalanine peptide and analogues were prepared by dissolving the lyophilized form of the peptides in 1,1,1,3,3,3-hexafluoro-2-propanol (HFP, Sigma). To avoid any pre-aggregation, fresh stock solutions were prepared for each experiment.

Methods

A fresh stock solution of the diphenylalanine peptide was dissolved in HFP to a concentration of 100 mg/mL. The stock solution was then diluted to a final concentration of 2 mg/mL in 20% ferrofluid diluted in water (EMG 508, Ferrotec Corporation). This commercially available water based ferrofluid carry 1.07% magnetite ($Fe_3O_4$) particles with a characteristic diameter of 10 nm in the presence of a stabilized anionic surfactant.

After dilution on water, the final concentration of the magnetite nanoparticles was 0.214%. After overnight incubation, self-assembly if the nanostructures was established. A 10-μl drop of the solution was deposited on a cover slip slide.

In the next step, the slide was placed in a permanent magnet of 0.5 T taken from a Hall Measurement System (Bridge Technology, USA). The sample was exposed to the external magnetic force until the solution was dried; this was followed by SEM analysis of the sample as described above.

For TEM analysis a 10-μl aliquot of the peptide solution was placed on a 200-mesh copper grid, covered by carbon stabilized Formvar film. After 1 minute, excess fluid was removed and the grid and samples were viewed using a JEOL 1200EX transmission electron microscope (TEM) operating at 80 kV.

Results

FIGS. 10a-10g present the self-assembly of the diphenylalanine-based peptide nanotubes in the presence of a ferrofluid and their exposure to an external magnetic field resulted in the control over their horizontal alignment.

FIG. 10a is a schematic illustration of the dipeptide monomers self-assembled in the presence of ferrofluid solution containing magnetite nanoparticles. As shown, diphenylalanine monomers were assembled in the presence of magnetite nanoparticles.

FIG. 10b is a TEM image of a self-assembled peptide nanostructure coated with magnetic particles. While the aromatic dipeptide nanostructures assembled into tubular structures, the magnetic nanoparticles formed a non-covalent coating layer of magnetic nanoparticles. The coating was peripheral about the walls of the non charged nanostructures. It is believed that the magnetite particles adhere to the walls by hydrophobic interactions. The presence of the magnetic particles did not affect the high yield of tube formation. The high efficiency of the process was observed by TEM analysis as all tubular structures were coated with magnetic particles.

FIG. 10c is a low-magnification SEM micrograph of the self-assembled magnetic nanostructures. The coated aromatic dipeptide nanostructures spread randomly when applied onto a surface.

FIG. 10d is a low-magnification SEM showing horizontal arrangement of the self-assembled magnetic nanostructure following their exposure to the magnetic field. As shown, upon exposure to an external magnetic field, all nanostructures responded to the field, resulting in spatial organization of the nanostructures onto a surface and their alignment according to the direction of the magnetic field.

FIG. 10e-10g are schematic illustrations of a self-assembled coated nanostructures (FIG. 10e), several coated nanostructures randomly oriented before exposed to the magnetic field (FIG. 10f), and horizontally aligned coated nanostructures while and following their exposure to a magnetic field.

ADDITIONAL REFERENCES

[1] Zhrong, Z. H., Wang, D. L., Cui, Y., Bockrath, M. W. & Lieber, C. M. Nanowire crossbar arrays as address decoders for integrated nanosystems. *Science* 302, 1377-1379 (2003).
[2] Kol, N. et al. Self-assembled peptide nanotubes are uniquely rigid bioinspired supramolecular structures. *Nano Lett.* 5, 1343-1346 (2005).
[3] Yemini, M., Reches, M., Rishpon, J. & Gazit, E. Novel electrochemical biosensing platform using self-assembled peptide nanotubes. *Nano Lett.* 5, 183-186 (2005).
[4] Terrones, M. et al. Controlled production of aligned-nanotube bundles. *Nature* 388, 52-55 (1997).
[5] Melosh, N. A. et al. Ultrahigh-density nanowire lattices and circuits. *Science* 300, 112-115 (2003).
[6] Huang, Y., Duan, X. F., Wei, Q. Q. & Lieber C. M. Directed assembly of one-dimensional nanostructures into functional networks. *Science* 291, 630-633 (2001)
[7] Thurn-Albrecht, T. et al. Ultrahigh-density nanowire arrays grown in self-assembled diblock copolymer templates. *Science* 290, 2126-2129 (2000).
[8] Song, Y. J. et al. Synthesis of peptide-nanotube platinum-nanoparticle composites. *Chem. Commun.* 1044-1045 (2004).
[9] Gorbitz, C. H. Nanotube formation by hydrophobic dipeptides. *Chem. Eur. J.* 7, 5153-5159 (2001).
[10] Gorbitz, C. H. The structure of nanotubes formed by diphenylalanine, the core recognition motif of Alzheimer's beta-amyloid polypeptide. *Chem. Commun.* 2332-2334 (2006).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of fabricating a nanostructure array, the method comprising dispensing on a substrate a solution of uncapped phenylalanine-phenylalanine dipeptides dissolved in an organic volatile solvent, and evaporating said solvent while generating conditions for self assembling of said peptide monomers such as to form peptide nanostructures arranged generally perpendicularly on said substrate, each of said peptide nanostructures being comprised of phenylalanine-phenylalanine peptides, wherein said substrate is a siliconized glass and said organic volatile solvent is hexafluoroisopropanol.

2. The method of claim 1, wherein said phenylalanine-phenylalanine peptides are dissolved in said organic volatile solvent at a concentration of at least 10 mg/ml.

3. The method of claim 1, wherein said nanostructure array comprises at least 10 elongated peptide nanostructures.

4. The method of claim 1, wherein said nanostructures are self-supported.

* * * * *